United States Patent
Adachi

(10) Patent No.: US 8,839,476 B2
(45) Date of Patent: Sep. 23, 2014

(54) ORAL CARE APPARATUS APPLIED TO THE REMOVAL OF DENTAL PLAQUE

(75) Inventor: Yuma Adachi, Kyoto (JP)

(73) Assignee: Omron Healthcare Co., Ltd., Kyoto (JP)

(*) Notice: Subject to any disclaimer, the term of this patent is extended or adjusted under 35 U.S.C. 154(b) by 0 days.

(21) Appl. No.: 14/237,817

(22) PCT Filed: Jun. 7, 2012

(86) PCT No.: PCT/JP2012/064626
§ 371 (c)(1),
(2), (4) Date: Feb. 7, 2014

(87) PCT Pub. No.: WO2013/027462
PCT Pub. Date: Feb. 28, 2013

(65) Prior Publication Data
US 2014/0199651 A1 Jul. 17, 2014

(30) Foreign Application Priority Data
Aug. 24, 2011 (JP) .................. 2011-182263

(51) Int. Cl.
*A61C 17/22* (2006.01)
*A61B 5/00* (2006.01)

(52) U.S. Cl.
CPC ............. *A61B 5/0088* (2013.01); *A61C 17/221* (2013.01); *A61C 17/224* (2013.01)
USPC .................. 15/22.1; 15/105; 433/27; 433/29; 433/32; 433/215

(58) Field of Classification Search
CPC .................................. A61C 17/16; A61C 17/22
USPC ........... 15/21.1, 22.1, 22.2, 22.4, 23, 28, 105; 433/27, 29, 32, 215
See application file for complete search history.

(56) References Cited

U.S. PATENT DOCUMENTS 6,485,300 B1 11/2002 Muller et al.
6,760,945 B2 * 7/2004 Ferber et al. ................... 15/22.2

(Continued)

FOREIGN PATENT DOCUMENTS

JP   A-2000-504605   4/2000
JP   A-2001-145645   5/2001

(Continued)

OTHER PUBLICATIONS

Homepage of Dental Detection-Dedicated Dental Wireless Intraoral Camera "Einstein Stella plaque," http://www.rfsystemlab.com/product/dental/ein_plaque/index.html.

(Continued)

*Primary Examiner* — Monica Carter
*Assistant Examiner* — Michael Jennings
(74) *Attorney, Agent, or Firm* — Oliff PLC

(57) ABSTRACT

An oral care apparatus includes: a care member; an orientation detection unit; an area estimation unit; a light source that emits light having a predetermined wavelength to which plaque reacts; a photoelectric conversion unit that receives light and converts the received light into an electric signal; an image capture unit that causes the light source to irradiate the care area with light, and that obtains image data, based on the electric signal of light reflected from the care area that is converted by the photoelectric conversion unit; a plaque detection unit for detecting an amount of plaque in the care area, based on the image data obtained by the image capture unit; and a storage unit for storing, in a memory, the care area estimated by the area estimation unit and the amount of plaque in the care area detected by the plaque detection unit in association with each other.

11 Claims, 21 Drawing Sheets

(56) References Cited

U.S. PATENT DOCUMENTS

| | | | |
|---|---|---|---|
| 6,799,967 B2* | 10/2004 | Cao | 433/29 |
| 6,954,961 B2* | 10/2005 | Ferber et al. | 15/22.1 |
| 7,029,277 B2* | 4/2006 | Gofman et al. | 433/29 |
| 7,210,930 B2* | 5/2007 | Kovac et al. | 433/29 |
| 7,467,946 B2* | 12/2008 | Rizoiu et al. | 433/29 |
| 8,063,932 B2* | 11/2011 | Boyer et al. | 348/66 |
| 8,077,949 B2* | 12/2011 | Liang et al. | 382/128 |
| 8,106,600 B1* | 1/2012 | Fregoso | 315/291 |
| 8,145,325 B2* | 3/2012 | Taniguchi et al. | 607/134 |
| 8,159,352 B2* | 4/2012 | Jimenez et al. | 340/573.1 |
| 8,239,991 B2* | 8/2012 | Shimizu et al. | 15/22.1 |
| 8,262,390 B1* | 9/2012 | Levine | 433/89 |
| 8,270,689 B2* | 9/2012 | Liang et al. | 382/128 |
| 8,279,450 B2* | 10/2012 | Oota et al. | 356/601 |
| 8,291,537 B2* | 10/2012 | Gall et al. | 15/22.1 |
| 8,671,493 B2* | 3/2014 | Hilscher et al. | 15/22.1 |
| 8,740,490 B2* | 6/2014 | Kuo | 401/188 R |
| 2006/0183071 A1* | 8/2006 | Hsuch | 433/29 |
| 2007/0099148 A1* | 5/2007 | Wong et al. | 433/29 |
| 2007/0099155 A1* | 5/2007 | Baughman | 433/216 |
| 2007/0105069 A1* | 5/2007 | Yamagishi | 433/215 |
| 2007/0154869 A1* | 7/2007 | Yau et al. | 433/215 |
| 2009/0215015 A1* | 8/2009 | Chu | 434/238 |
| 2011/0159453 A1* | 6/2011 | Kotlarchik | 433/27 |
| 2012/0011667 A1* | 1/2012 | Kressner | 15/22.4 |
| 2012/0014572 A1* | 1/2012 | Wong et al. | 382/128 |
| 2012/0015330 A1* | 1/2012 | Zhivago | 433/215 |
| 2012/0028221 A1* | 2/2012 | Williams | 433/215 |
| 2012/0231420 A1* | 9/2012 | Wong et al. | 433/215 |
| 2012/0231421 A1* | 9/2012 | Boerjes et al. | 433/223 |
| 2012/0266397 A1* | 10/2012 | Iwahori | 15/22.1 |
| 2012/0301839 A1* | 11/2012 | Stoianovici et al. | 433/27 |
| 2013/0108981 A1* | 5/2013 | Duret | 433/30 |
| 2014/0065588 A1* | 3/2014 | Jacobson et al. | 434/263 |
| 2014/0072932 A1* | 3/2014 | Brawn et al. | 433/173 |

FOREIGN PATENT DOCUMENTS

| | | |
|---|---|---|
| JP | A-2001-170084 | 6/2001 |
| JP | A-2001-218624 | 8/2001 |
| JP | A-2002-515276 | 5/2002 |
| JP | A-2008-119154 | 5/2008 |
| JP | A-2008-532619 | 8/2008 |
| WO | WO 03092534 A2 * | 11/2003 |
| WO | WO 2006/046543 A1 | 5/2006 |
| WO | WO 2011/096285 A1 | 8/2011 |

OTHER PUBLICATIONS

Homepage of "Intraoral Camera 'MIHARU'," http://www.shinwa-musen.co.jp/camera3/miharu.html.
International Search Report issued in International Application No. PCT/JP2012/064626 on Sep. 11, 2012 (with translation).

* cited by examiner

FIG. 7

| AREA | PLAQUE AMOUNT (%) (DATE/TIME) | PLAQUE AMOUNT (%) (DATE/TIME) | PLAQUE AMOUNT (%) (DATE/TIME) |
|---|---|---|---|
| MAXILLARY ANTERIOR BUCCAL SIDE | 7 | 10 | 15 |
| MAXILLARY ANTERIOR LINGUAL SIDE | — | — | — |
| MAXILLARY LEFT BUCCAL SIDE | 12 | 20 | 15 |
| MAXILLARY LEFT LINGUAL SIDE | — | — | — |
| MAXILLARY RIGHT BUCCAL SIDE | — | — | — |
| MAXILLARY RIGHT LINGUAL SIDE | — | — | — |
| MANDIBULAR ANTERIOR BUCCAL SIDE | — | — | — |
| MANDIBULAR ANTERIOR LINGUAL SIDE | — | — | — |
| MANDIBULAR LEFT BUCCAL SIDE | 12 | 15 | 15 |
| MANDIBULAR LEFT LINGUAL SIDE | — | — | — |
| MANDIBULAR RIGHT BUCCAL SIDE | — | — | — |
| MANDIBULAR RIGHT LINGUAL SIDE | — | — | — |

ORAL CARE APPARATUS APPLIED TO THE REMOVAL OF DENTAL PLAQUE

TECHNICAL FIELD

This invention relates to an oral care apparatus, and particularly relates to an oral care apparatus applied to the removal of dental plaque.

BACKGROUND ART

Conventionally, electric toothbrushes that operate with a vibration that is appropriate for removing plaque have been proposed. It is desirable for a user of an electric toothbrush that information relating to where plaque is attached, whether plaque is removed by brushing, and the like is provided.

In order to fulfill this desire, in Patent Literature 1 (JP 2001-145645A) and Patent Literature 2 (JP 2001-170084A), a video scope and a toothbrush are integrally provided, and an image of teeth captured during brushing is displayed.

Also, in Patent Literature 3 (JP 2001-218624A), an image of teeth that are being brushed is captured with a camera incorporated in the brush portion of a toothbrush, and the image thereof is displayed.

Also, Patent Literature 4 (JP 2008-119154A) proposes a function of collecting attached substances removed from the oral cavity with a cleaning tool, and facilitating the checking of whether attached substances have been removed.

Also, in Patent Literature 5 (JP 2008-532619A), it is possible to adjust the power or operations of a toothbrush in accordance with information received by a sensor. Furthermore, Patent Literature 5 describes a configuration in which light is emitted from a toothbrush in order to carry out optical whitening and the like using a photochemical effect.

With these Patent Literatures, it is not possible to check an area unbrushed by a toothbrush, that is, a tooth where plaque remains. In contrast, the homepage of Non-Patent Literature 1 "Einstein Stella plaque" ((RF Co., Ltd.) http://www.rfsystemlab.com/product/dental/ein_plaque/index.html) and the homepage of Non-Patent Literature 2 "Intraoral Camera "MIHARU"" (http://www.shinwa-musen.co.jp/camera3/miharu.html) propose a wireless intraoral camera. The intraoral camera emits light having a predetermined wavelength to which only plaque and resin react, receives the light reflected therefrom, and converts signals of the received light into video signals to be output as video images. The intraoral camera thus has a function of providing information on an unbrushed area of teeth in video image form.

CITATION LIST

Patent Literature

Patent Literature 1: JP2001-145645A
Patent Literature 2: JP2001-170084A
Patent Literature 3: JP2001-218624A
Patent Literature 4: JP2008-119154A
Patent Literature 5: JP2008-532619A

Non-Patent Literature

Non-Patent Literature 1: Homepage of Dental Detection-Dedicated Dental Wireless Intraoral Camera "Einstein Stella plaque", [online], retrieved on Dec. 20, 2008, from URL: http://www.rfsystemlab.com/product/dental/ein_plaque/index.html Non-Patent Literature 2: Homepage of "Intraoral Camera "MIHARU"" dedicated dental camera and monitor for a dentist, [online], retrieved on Dec. 20, 2008, from http://www.shinwa-musen.co.jp/camera3/miharu.html

SUMMARY OF INVENTION

Technical Problem

According to Non-Patent Literatures 1 and 2, it is possible to check unbrushed areas, with a captured video image. However, in the case of brushing teeth in the unbrushed area, it is necessary for a user to estimate the unbrushed area in the dentition from only the captured video image, and to press the toothbrush against that area, so therefore it is difficult to estimate the area from only a captured video image. Also, it is difficult to grasp the amount of unbrushed plaque from the captured video image, and therefore brushing is not sufficiently performed and plaque remains, or excess brushing may cause scratches on the surfaces of teeth. Therefore, a function of automatically detecting an intraoral area requiring care and the amount of plaque remaining in the care area and managing them in association with each other is desirable.

It is an object of the present invention to provide an oral care apparatus that stores data on a care area in the oral cavity and the amount of plaque detected in correspondence with the care area.

Solution to Problem

An oral care apparatus according to this invention includes: a care member for caring for an oral cavity; an orientation detection unit for detecting an orientation of the care member; an area estimation unit for estimating a care area in the oral cavity, based on the detected orientation; a light source that emits light having a predetermined wavelength to which plaque reacts; a photoelectric conversion unit that receives light and converts the received light into an electric signal; an image capture unit that causes the light source to irradiate the care area with light, and that obtains image data, based on the electric signal of light reflected from the care area that is converted by the photoelectric conversion unit; a plaque detection unit for detecting an amount of plaque in the care area, based on the image data obtained by the image capture unit; and a storage unit for storing, in a memory, the care area estimated by the area estimation unit and the amount of plaque in the care area detected by the plaque detection unit in association with each other.

Advantageous Effects of Invention

According to the present invention, it is possible to automatically detect an area requiring care in the oral cavity and the amount of plaque in the care area, store data on them in a memory and manage them in association with each other.

BRIEF DESCRIPTION OF DRAWINGS

FIG. 7 is a diagram illustrating an example of a table that stores the amount of plaque in each area according to the present embodiment.

DESCRIPTION OF EMBODIMENTS

Figure 1:
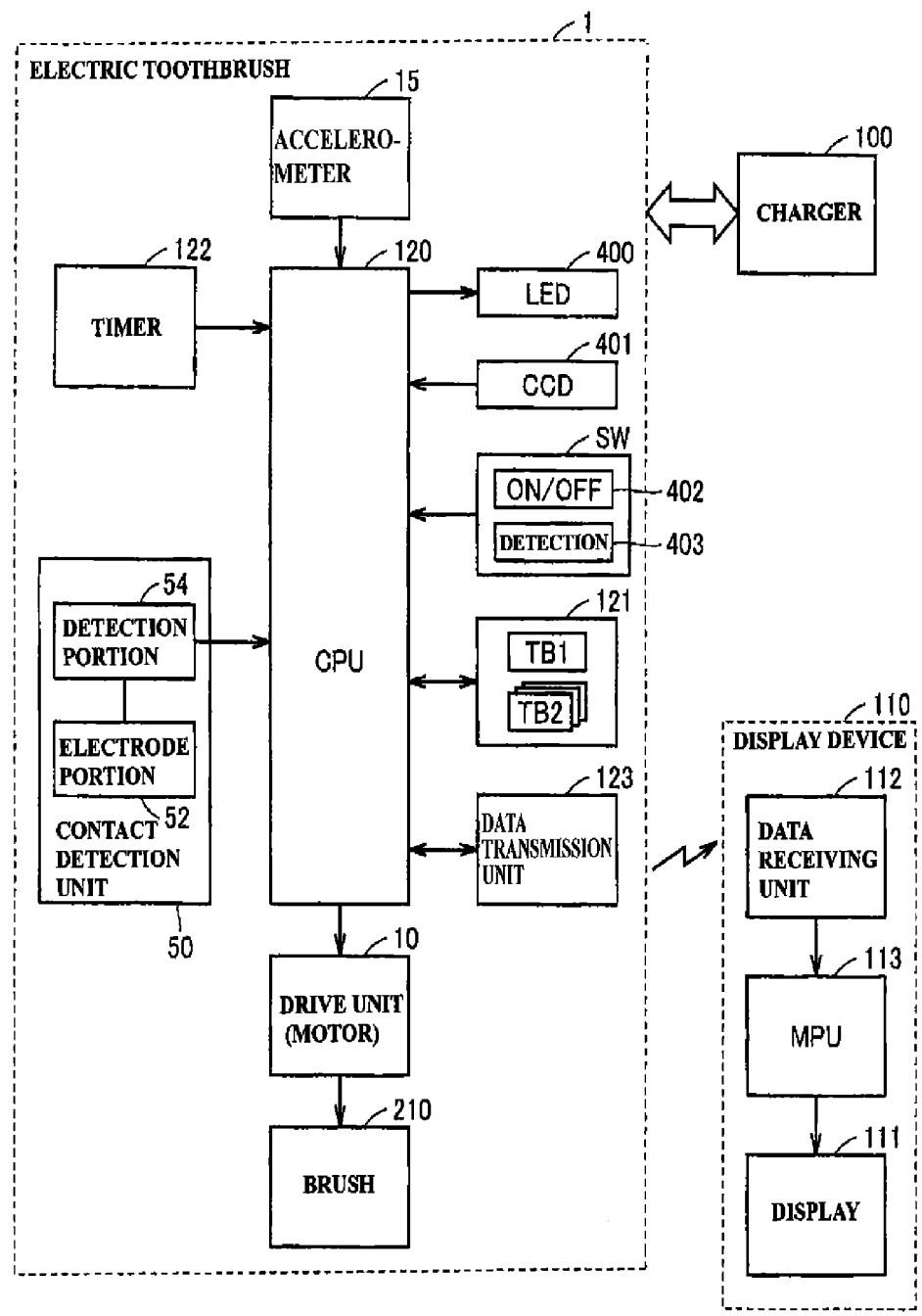
FIG. 1 is a block diagram illustrating a system including an electric toothbrush according to the present embodiment.

Embodiments of the present invention will be described hereinafter with reference to the drawings. Note that the same reference numerals indicate identical or corresponding areas of the drawings.

Although the embodiment describes an electric toothbrush having a brush implanted in the surface of a housing, the configuration of the embodiment can be applied generally in apparatuses capable of being used in oral care (cleaning teeth, brushing, or the like). Specifically, the embodiment can be applied in an apparatus that employs, as a material used in oral care, a resinous component such as a sponge, rubber, an elastomer, or the like in place of a toothbrush, or an oral care member in which such a resinous component is combined with a brush.

Configuration

The configuration of an electric toothbrush will be described with reference to FIGS. 1 through 3.

FIG. 1 shows a block diagram illustrating a system including the electric toothbrush; FIG. 2 shows the external appearance of the electric toothbrush; and FIG. 3 shows the internal configuration of the electric toothbrush.

An electric toothbrush 1 includes a main body portion 2 that includes a motor 10 serving as a drive source, and a vibrating member 5 that periodically moves (vibrates) in conjunction with the rotation of the motor 10 and that serves as a vibration source. Therefore, the rotational period of the motor 10 corresponds to the period of vibration (movement) of an electric toothbrush main body. The main body portion 2 has a substantially columnar housing, and a portion of the housing functions as a handle portion that a user holds, that is, a user grips with his/her hand, when brushing his/her teeth.

Furthermore, with regard to the electric toothbrush 1, a charger 100 in which the main body portion 2 is mounted and that is used for charging the electric toothbrush 1 when placed thereon, and a display device 110 for outputting various types of information such as a brushing result are provided.

The housing of the main body portion 2 includes a switch SW that a user operates to input an instruction and that receives operations from the outside. The switch SW includes a switch 402 for turning the power on and off, a switch for switching between operating modes of the motor 10 described later, and a switch 403 for giving an instruction to start detecting plaque.

The housing of the main body portion 2 is provided with the motor 10 (for example, a direct current motor), a driving circuit 12, a rechargeable battery 13 that serves as a power source with a rated output of 2.4 V for supplying power to the various constituent elements, a charging coil 14, and so on. The rechargeable battery 13 is charged simply by placing the main body portion 2 in the charger 100, via non-contact charging through electromagnetic induction. The driving circuit 12 includes a CPU (Central Processing Unit) 120, which is mounted on a substrate (not shown), that executes various types of computations and control, a memory 121 that stores tables TB1 and TB2 shown in FIGS. 7 and 23 that are described later, programs, and various types of configuration values, a timer 122 that measures time and outputs data on measurement time, a data transmission unit 123, and so on.

The data transmission unit 123 carries out wireless communication with a data receiving unit 112 of the display device 110. The display device 110 includes a data receiving unit 112, an MPU (Micro Processing Unit) 113, and a display 111. The display 111 outputs various types of data such as brushing results received by the data receiving unit 112, processing results in the MPU 113, and so on.

Figure 4:
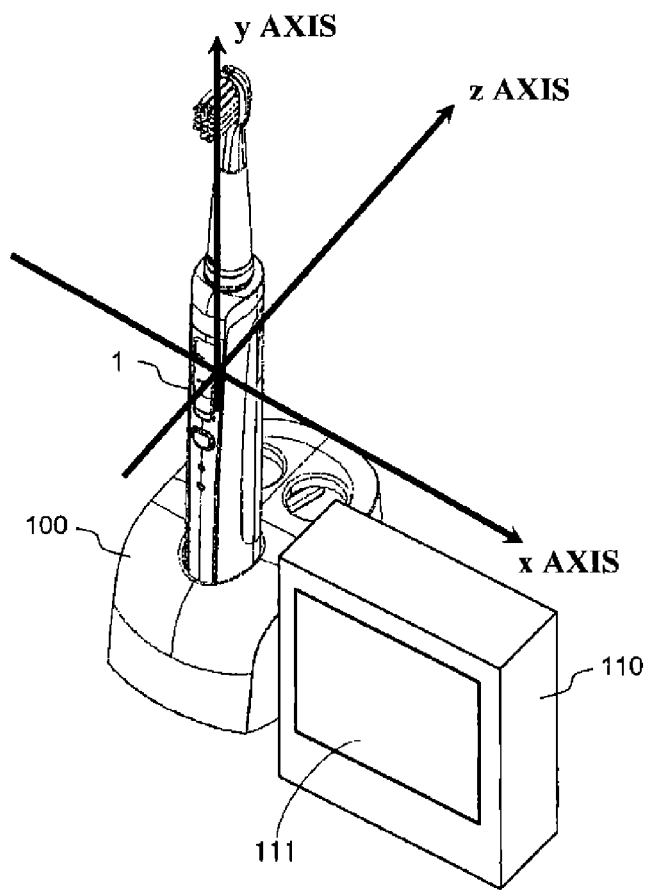
FIG. 4 is a diagram illustrating axes related to acceleration vectors of the electric toothbrush according to the present embodiment.

Furthermore, a multi-axis (here, three axes, or x, y, and z axes) accelerometer 15, for example, is provided within the main body portion 2 in order to detect the orientation of the electric toothbrush 1. As shown in FIG. 4, the accelerometer 15 is installed so that the x axis is parallel to a brush surface, the y axis matches the lengthwise direction of the main body portion 2, and the z axis is perpendicular to the brush surface. In other words, when the main body portion 2 has been placed in the charger 100, the gravity acceleration vector is parallel to the y axis, when the brush surface is pointed upward, the gravity acceleration vector is parallel to the z axis, and when the main body portion 2 is placed horizontally and the brush surface is pointed sideways, the gravity acceleration vector is parallel to the x axis. The outputs of the axes of the accelerometer 15 are inputted into the CPU 120, and are used to detect a three-dimensional orientation of the brush 210.

A piezoelectric resistance-type, an electrostatic capacitance-type, or a thermal detection-type micro electro mechanical systems (MEMS) sensor can be used favorably as the accelerometer 15. MEMS sensors are extremely small and can therefore easily be incorporated into the main body portion 2. However, the type of the accelerometer 15 is not limited thereto, and an electrokinetic sensor, a strain gauge sensor, a piezoelectric sensor, or the like may be used instead. In addition, although not particularly shown, it is beneficial to provide correction circuits for correcting the balance of sensitivities, temperature characteristics of the sensitivities, temperature drift, and so on of the sensors in the respective axes. Furthermore, a band pass filter (low-pass filter) for removing dynamic acceleration components, noise, and so on may be provided. Further still, noise may be reduced by smoothing the waveforms of the outputs from the accelerometer.

The main body portion 2 accommodates an LED (Light Emitting Diode) 400 corresponding to a light source that emits light having a predetermined wavelength (ultraviolet light at 405 nm) to which plaque reacts, and a CCD (Charge Coupled Device) 401 that serves as a photoelectric conversion element that receives light, converts the received light into an electric signal that corresponds to the amount of received light, and outputs the converted electric signal.

Here, when the inside of an oral cavity is irradiated with light having a predetermined wavelength using the LED 400, only plaque or resin reacts to the light emitted, and the light that is reflected from the plaque or resin as a result of the reaction and that has a red wavelength (635 nm) enters the CCD 401. The CCD 401 receives light, and outputs an electric signal corresponding to the amount of received light as an image signal.

Here, although the CCD 401 is used as an image sensor that serves as a photoelectric conversion element of a PD (Photo Diode), a CMOS (Complementary Metal Oxide Semiconductor) image sensor may be used in place of the CCD 401.

The vibrating member 5 includes a stem portion 20 that is anchored to the main body portion 2 and a brush component 21 that is mounted to the stem portion 20. Brush 210 is implanted in the distal end of the brush component 21. The brush component 21 is a consumable item, and is thus configured so as to be removable from the stem portion 20 for replacement.

The brush component 21 of the vibrating member 5 includes a brush portion 3 in which the brush 210 is disposed and a shank portion 4 located toward the main body portion 2. Although the present embodiment illustrates a configuration in which the brush component 21 that includes the comparatively long shank portion 4 can be replaced, it should be noted that the configuration may be such that only the brush portion 3, or a brush component that includes the brush portion 3 and a short shank portion, can be replaced. In other words, the configuration may be such that part or all of the shank portion is included as part of the main body.

The stem portion 20 is configured of a resin material. The stem portion 20 is attached to the main body portion 2 via an elastic member 202 configured of an elastomer. The stem portion 20 is a closed-ended (on the brush-side end) cylindrical member, and has a shaft bearing 203 at a distal end within the cylinder. The distal end of an eccentric shaft 30 that is linked to a rotating shaft 11 of the motor 10 is inserted into the shaft bearing 203 of the stem portion 20. This eccentric shaft 30 has a weight 300 in the vicinity of the shaft bearing 203, and thus the center of gravity of the eccentric shaft 30 is offset from the rotational center thereof. Note that a minute clearance is provided between the distal end of the eccentric shaft 30 and the shaft bearing 203.

The electric toothbrush 1 further includes an electrode-based contact detection unit 50 for detecting contact or proximity. The contact detection unit 50 detects contact with or proximity to the human body, or in other words, the cheek mucosa and the tongue, during brushing. Specifically, the contact detection unit 50 includes an electrode portion 52 and a detection portion 54 for detecting an impedance from the electrode portion 52.

The electrode portion 52 includes an electrode 521 disposed on the rear surface of the brush portion 3 (the surface on the opposite side of the surface to which the brush 210 is attached) (also called a "rear surface electrode" hereinafter) and an electrode 522 disposed on the main body portion 2 (also called a "main body electrode" hereinafter). It is desirable for the main body electrode 522 to be provided on the rear surface of the main body portion 2 so as to be in continuous contact with the hand of the user during brushing. This is because the principle of action/reaction dictates that it is necessary for a force to be applied to the rear surface of the main body portion 2. The main body electrode 522 may be extended so as to be aligned with a fingertip of the user. The detection portion 54, meanwhile, may be installed within the driving circuit 12.

The rear surface electrode 521 and the main body electrode 522 may employ a conductive resin material, and may be formed integrally with the members to which they are respectively attached. According to this structure, there is no gap between the members, which makes it possible to ensure water resistance with ease and reduce the buildup of grime. The electrodes may also be formed of metal sheets, or may be formed as thin films through spray coating. The electrodes 521 and 522 may also be provided with recesses and protrusions in order to increase the surface areas thereof. Providing recesses and protrusions also guards against slippage. The recesses and protrusions may be of any shapes.

Figure 3:
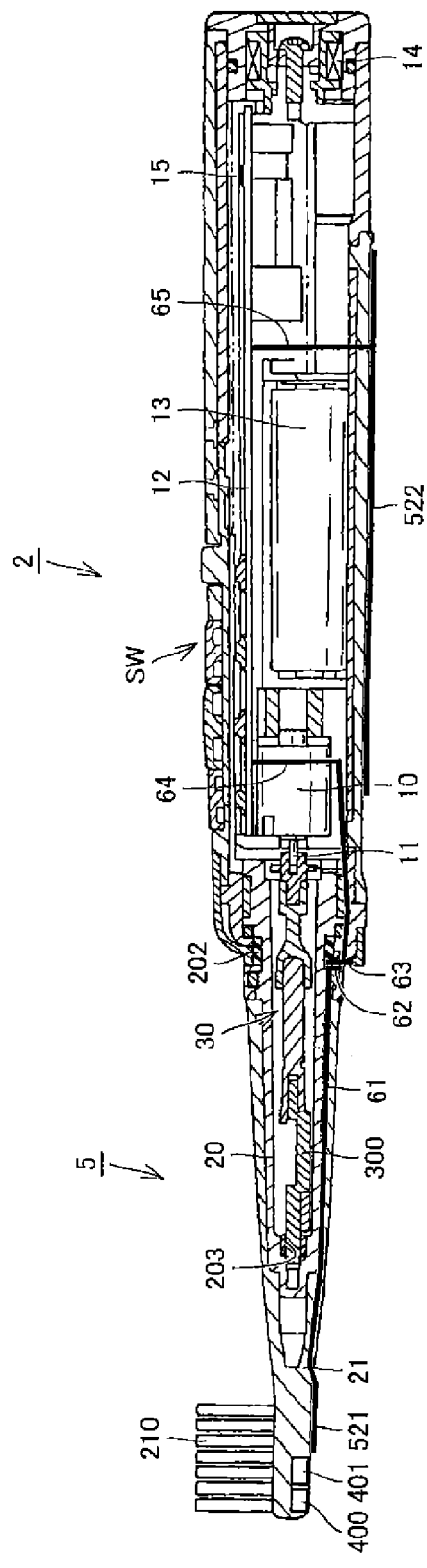
FIG. 3 is a diagram of the internal configuration of the electric toothbrush according to the present embodiment.

As shown in FIG. 3, the rear surface electrode 521 is formed integrally with an electrode 61 that is formed within the replaceable brush component 21 and a contact electrode 62 that is exposed at an end of the brush component 21 (that is, the surface that makes contact with the main body portion 2). The contact electrode 62 functions as a terminal for an electric connection between the main body portion 2 and the rear surface electrode 521. A contact electrode 63 is provided on an end surface of the main body portion 2 (on the side that is connected to the brush component 21). The contact electrode 63 is electrically connected to the driving circuit (substrate) 12 by a lead wire 64. The main body electrode 522 is electrically connected to the driving circuit (substrate) 12 by a lead wire 65.

Figure 2:
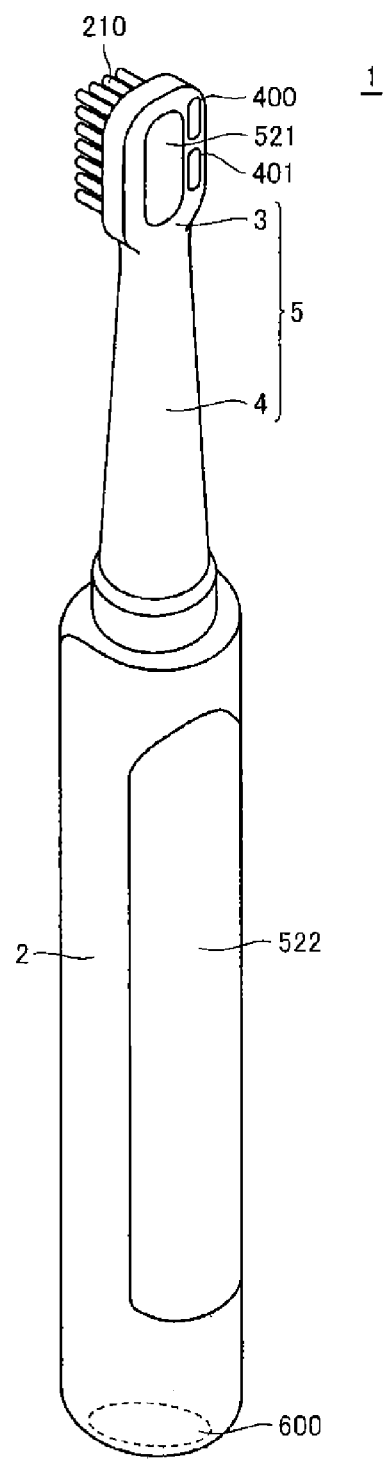
FIG. 2 is the external appearance of the electric toothbrush according to the present embodiment.

These electrical components (the electrodes 61, 62, 63 and the lead wires 64 and 65) for electrically connecting the rear surface electrode 521 and the main body electrode 522 shown in FIG. 2 are also included in the electrode portion 52 shown in FIG. 1. The detection portion 54 within the driving circuit 12 is capable of detecting an impedance by detecting a current that flows through the electric circuit configured by the electrode portion 52.

Also, a light emitting surface of the LED 400 and a light receiving surface of the CCD 401 shown in FIG. 1 are attached to the same surface as that of the rear surface electrode 521, which is the rear surface of the surface to which the brush 210 is attached. The light emitting surface of the LED 400 and the light receiving surface of the CCD 401 are covered and protected by a light transmissive member (not shown). The LED 400 and the CCD 401 are connected to a wiring pattern of a substrate on which the CPU 120 is mounted via a lead wire (not shown). Accordingly, light emitting operations of the LED 400 are controlled by signals sent from the CPU 120, and the electric signals generated through photoelectric conversion in the CCD 401 are output to the CPU 120.

In the case where the configuration is such that only the brush portion 3 or the portion in the vicinity thereof is replaceable as described above, the rear surface electrode may be attached to the shank portion on the main body-side. Doing so makes it possible to simplify the internal configuration of the electrode portion, and also makes it possible to reduce costs when replacing the brush component.

Alternatively, the rear surface electrode 521, the LED 400 and the CCD 401 may be made attachable to and detachable from the brush component 21. Doing so makes it possible to reuse the rear surface electrode 521, the LED 400 and the CCD 401 when replacing the brush component 21.

It should be noted that depending on the materials of the components within the main body potion 2 and the materials of the main body portion 2 itself, it is possible to configure a closed loop that passes through the human body even without providing the main body electrode 522, and thus the main body electrode 522 need not be included in the electrode portion 52.

Example of Another Arrangement of Optical Element

Although in FIG. 2, the LED 400 and the CCD 401 are mounted on the rear surface of the brush 210 so that the emission and reception of light are not blocked by the bristles and so as not to become dirty with plaque removed by brushing, the mounting position is not limited to the rear surface.

Figure 5:
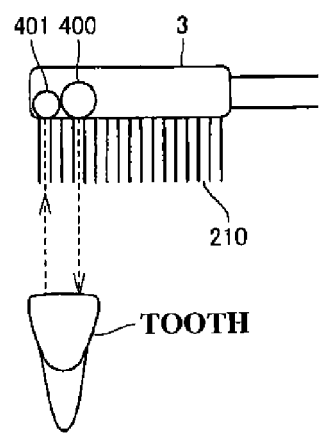
FIG. 5 is a diagram illustrating an example of another arrangement of an optical element according to the present embodiment.

For example, in the case where the bristles of the brush 210 are made of a material transmitting light having wavelengths corresponding to the wavelengths of the emitted light and received light, the LED 400 and the CCD 401 may be disposed on the side of the surface in which the brush 210 is implanted, as shown in FIG. 5.

Note that the LED 400 and the CCD 401 are not limited to a LED and a CCD that are disposed adjacent to the vicinity of the brush 210 that serves as a care member, as described above. They may be provided on the end of the columnar main body portion 2 in the longitudinal direction opposite from the end thereof on which the brush 210 is provided (see an end 600 shown in FIG. 2). In other words, in the case of using the toothbrush for the purpose of capturing an image of a desired area inside the oral cavity and checking the image and the amount of plaque, independently of a care area during brushing, they may be provided at positions other than that of the brush 210, such as the end 600.

Functional Configuration

Figure 6:
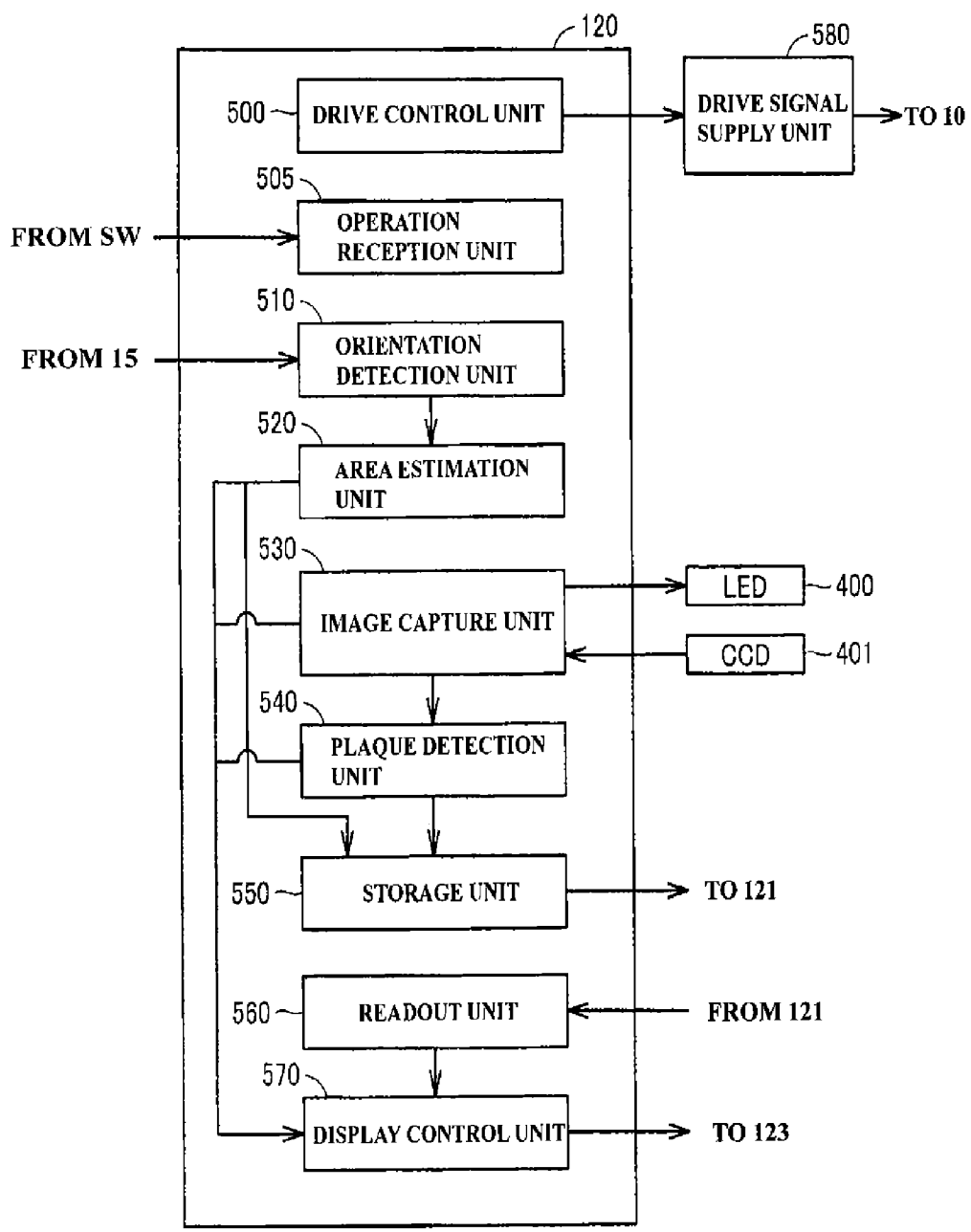
FIG. 6 is a diagram of the functional configuration of the electric toothbrush according to the present embodiment.

The functional configuration of the electric toothbrush 1 will be described with reference to FIG. 6. FIG. 6 shows functions of the CPU 120 in relation to the corresponding peripheral circuits and portions. Although it is assumed that the functions of the CPU 120 that are shown in FIG. 6 are realized by the CPU 120 reading out and executing programs stored in the memory 121 in advance, they may be realized by combinations of programs and circuits.

The CPU 120 of the electric toothbrush 1 includes: a drive control unit 500 for controlling a drive signal supply unit 580 that supplies drive signals to the motor 10; an operation reception unit 505 that detects that the switch SW has been operated and that outputs operation signals in accordance with the operated switches; an orientation detection unit 510 for detecting the orientation of a brush portion 3 including the brush 210 that serves as a care member; an area estimation unit 520 for estimating a brushing (care) area based on the detected orientation; an image capture unit 530; a plaque detection unit 540 for detecting the amount of plaque in the estimated area; a storage unit 550 for storing the estimated area and the amount of plaque detected in correspondence with the area in a table TB1 of the memory 121; a readout unit 560 for reading out data from the memory 121; and a display control unit 570 that outputs the readout data to a data transmission unit 123 for displaying the data in the display device 110.

The image capture unit 530 controls the LED 400 such that light is emitted therefrom when the operation reception unit 505 outputs an operation signal based on the switch 403 being operated. The CCD 401 receives light that is emitted from the LED 400 and reflected from the oral cavity, and an image signal obtained through photoelectric conversion is output to the image capture unit 530. The image capture unit 530 performs noise removal (filter processing) on the input image signal and converts it into gradation values to obtain image data, which is digital data. Operations from when light is caused to be emitted from the LED 400 to when image data is obtained through photoelectric conversion as a result of the CCD 401 receiving light are referred to as "image capture".

The plaque detection unit 540 detects the amount of plaque in a care area based on the image data obtained by image capture. Specifically, the gradation value of each pixel in image data is compared with a predetermined threshold. The predetermined threshold includes a gradation value corresponding to the image of teeth and a gradation value corresponding to the image of plaque (red). Therefore, based on the comparison result, it is possible to detect the sizes of the region of teeth and the region of a plaque portion in the image obtained by image capture of the care area. The plaque detection unit 540 calculates ((the size of the region of a plaque portion/the size of the region of teeth)×100) (unit: percentage), as the amount of plaque.

Principles of Driving Electric Toothbrush

The drive control unit 500 outputs a control signal corresponding to the operating mode to the drive signal supply unit 580. The drive signal supply unit 580 generates a drive signal (for example, a pulse width-modulated signal) based on the input control signal, and supplies the generated drive signals to the motor 10. Here, the control signal is a signal for specifying a period and a Duty ratio for the drive signal. The drive signal supply unit 580 generates a drive signal that is a pulse having a width corresponding to the period and the Duty ratio specified by the control signal, and continuously supplies the drive signal to the motor 10. The periodic pulse signal is continuously supplied to the motor 10, and thereby the rotation period of the motor 10 is controlled.

Although, when the rotating shaft 11 of the motor 10 rotates due to the drive signal, the eccentric shaft 30 also rotates along with the rotation of the rotating shaft 11, the rotating shaft 11 of the motor 10 moves in gyrations central to the rotational center because the center of gravity of the eccentric shaft 30 is offset. Accordingly, the movement of the distal end of the eccentric shaft 30 is transmitted to the inner wall of the shaft bearing 203, which causes the stem portion 20 and the brush component 21 attached thereto to periodically move (vibrate) at a high rate of speed. In other words, the motor 10 serves as a drive source that causes the brush 210 to move, and the eccentric shaft 30 serves as a motion transmission mechanism (motion conversion mechanism) that converts the output of the motor 10 (that is, rotation) into vibration of the vibrating member 5 that serves as a vibration source. Here, the rotation of the motor 10 is converted to the periodic movement of the brush 210 that moves in conjunction therewith, and the periodic movement includes a vertical and horizontal reciprocating movement, a rotational movement, or the like due to the vibration of the brush 210.

The user can brush his or her teeth by gripping the main body portion 2 in his or her hand and pressing the brush 210, which is moving at a high rate of speed, against his or her teeth. Note that a configuration may be adopted in which the CPU 120 monitors the continuous operating time using the timer 122, and automatically stops the movement of the brush after a predetermined amount of time (for example, two minutes) has passed.

With the electric toothbrush 1 according to the present embodiment, the eccentric shaft 30, which serves as the motion transmission mechanism, is contained within the vibrating member 5, and the weight 300 in particular is disposed on the side of the vicinity of the brush 210. Therefore, the portion that includes the brush 210 can be caused to vibrate in an efficient manner. Meanwhile, the vibrating member 5 (the stem portion 20) is attached to the main body portion 2 via the elastic member 202, and thus the vibration of the vibrating member 5 is not easily transmitted to the main body portion 2. This makes it possible to reduce vibrations in the main body portion 2 and in the hand when brushing the teeth, which makes it possible to improve the comfort of use.

Operations of Electric Toothbrush

The manner in which food residue, plaque, and so on adheres to a tooth depends on the type of the tooth (in the maxilla/mandible, whether a molar/incisor, and so on), the area of the tooth (the lingual side/buccal side, the side surface/occlusal surface of the tooth, and so on). Accordingly, plaque caused by unbrushing differs for different areas of the dentition. In light of this, it is desirable to evaluate the amount of plaque that also serves as an evaluation value about whether or not proper brushing is being carried out on an area-by-area basis.

Accordingly, the electric toothbrush 1 according to the present embodiment estimates a brushing area based on the orientation of the brush as detected by the accelerometer 15 (orientation information) and detection results from the contact detection unit 50. The plaque detection unit 540 then detects the amount of plaque in each estimated area. The storage unit 550 stores, in the table TB1 of the memory 121, the brushing time and date, the estimated area, and the amount of plaque detected in correspondence with the area, in association with each other.

FIG. 7 is a diagram showing an example of a table TB1 that stores the amount of plaque in each area. Referring to FIG. 7, the amounts of plaque detected by the plaque detection unit 540 in correspondence with the estimated areas and the detected times and dates are stored in the table TB1 in association with each other. The time and date are obtained based on data on time measured by the timer 122.

Figure 8:
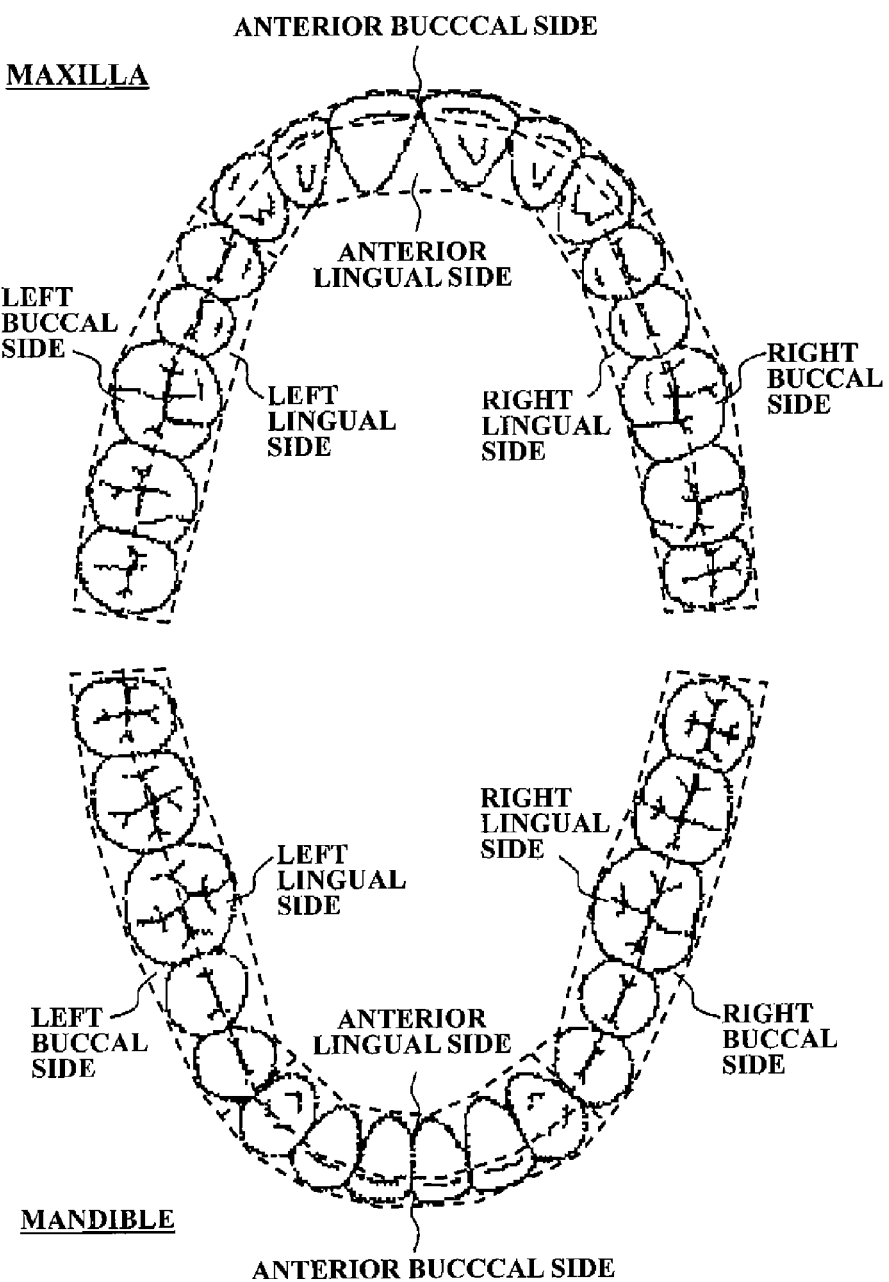
FIG. 8 is a diagram illustrating brushing areas according to the present embodiment.

Brushing areas will be described. In the present embodiment, as shown in FIG. 8, the upper dentition and lower dentition are segmented into 12 areas: a maxillary anterior buccal side; a maxillary anterior lingual side; a maxillary left buccal side; a maxillary left lingual side; a maxillary right buccal side; a maxillary right lingual side; a mandibular anterior buccal side; a mandibular anterior lingual side; a mandibular left buccal side; a mandibular left lingual side; a mandibular right buccal side; and a mandibular right lingual side. However, the segmentation of the dentition is not limited thereto, and broader or narrower segmentation may be carried out instead. For example, the upper and lower left and right occlusal surfaces may be taken into consideration as well.

Note that because the tongue is not present in the maxilla, the maxillary anterior lingual side, maxillary left lingual side, and maxillary right lingual side are given the more precise names of "maxillary anterior palatal side", "maxillary left palatal side", and "maxillary right palatal side", respectively. Likewise, because the cheeks are not present in the forward jaw area, the maxillary anterior buccal side and the mandibular anterior buccal side are given the more precise names of "maxillary anterior labial side" and "mandibular anterior labial side", respectively.

Figure 9:
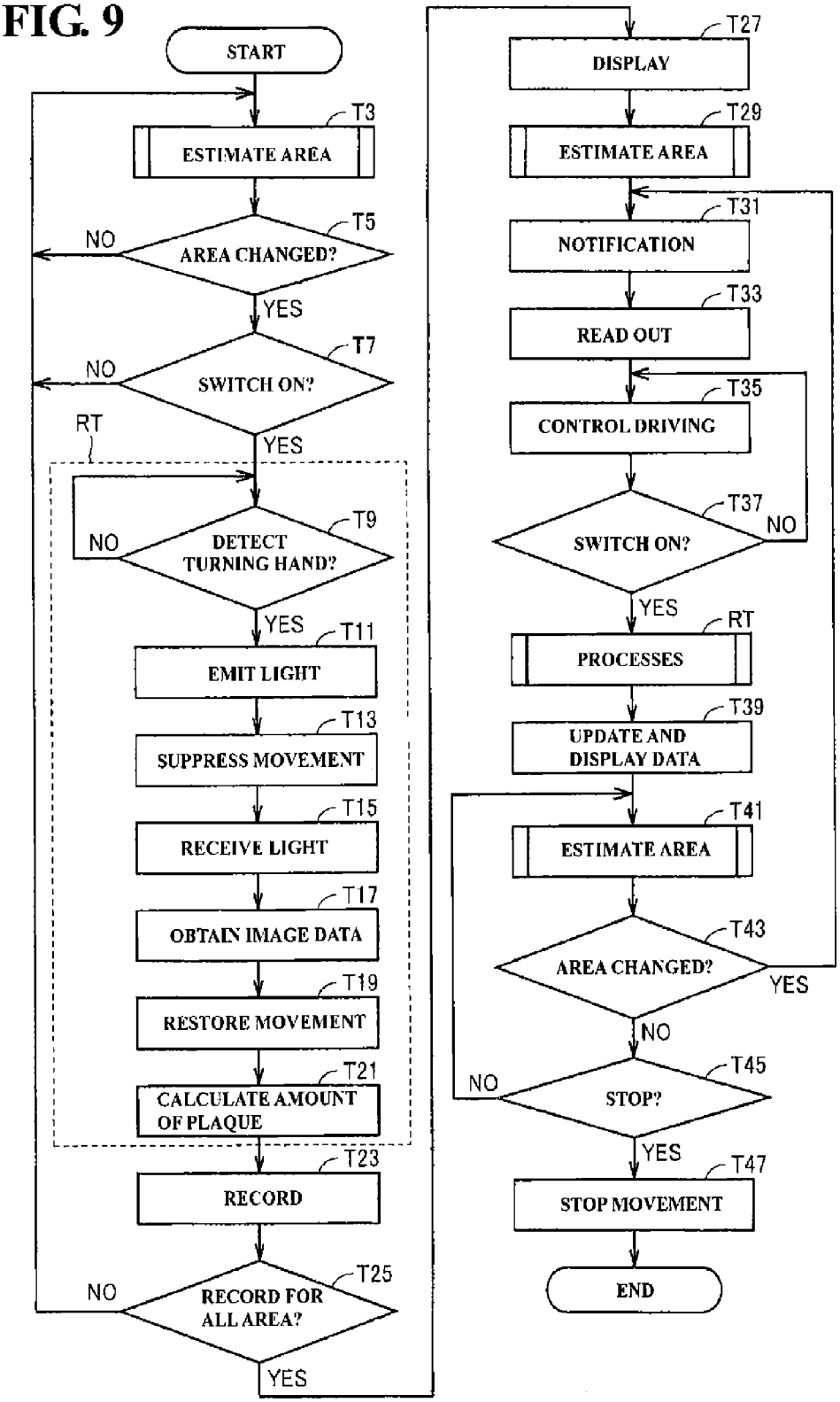
FIG. 9 is a flowchart of a main routine according to the present embodiment.

A flow of the brushing evaluation will be described in detail with reference to the flowcharts shown in FIGS. 9 through 13. FIG. 9 is a flowchart illustrating a main routine for evaluating brushing, whereas FIGS. 10 through 13 are flowcharts illustrating various processes in the main routine in detail. Note that unless explicitly mentioned otherwise, the processes described hereinafter are executed by the CPU 120 in accordance with programs stored in the memory 121.

Note that it is assumed that in the case of moving the brush 210 to a brushing area to detect the amount of plaque in the area, the user turns his/her hand that is holding the electric toothbrush 1 so that the brushing area is irradiated with the light emitted from the LED 400, in other words, so that the rear surface of the surface in which the brush 210 is implanted opposes the brushing area.

First, when the switch 402 of the switch SW of the electric toothbrush 1 is operated, an operating signal to turn on a power source is output from the operation reception unit 505, and the CPU 120 estimates a brushing area (step T3).

Estimation of brushing areas will be described with reference to flowcharts shown in FIGS. 10 to 13.

First, the orientation detection unit 510 detects the orientation (tilt) of the brush based on the output of the accelerometer 15 (step S (hereinafter, simply referred to as S) 10). Next, the area estimation unit 520 estimates the brushing area based at least on the orientation detected in S10, and outputs information on the estimated area (S20). The estimated area is temporarily stored in the memory 121. Also, the display control unit 570 outputs information on the estimated area to the display device 110 via the data transmission unit 123. In the display device 110, the information on the area is displayed on the display 111 (S60). Accordingly, the user can check a current brushing area. Also, information on the estimated areas is temporarily stored in the memory 121. Thereafter, the procedure returns to the processing shown in FIG. 9.

Hereinafter, the processes in S10 to S60 will be described in detail.

Orientation Detection

Figure 11:
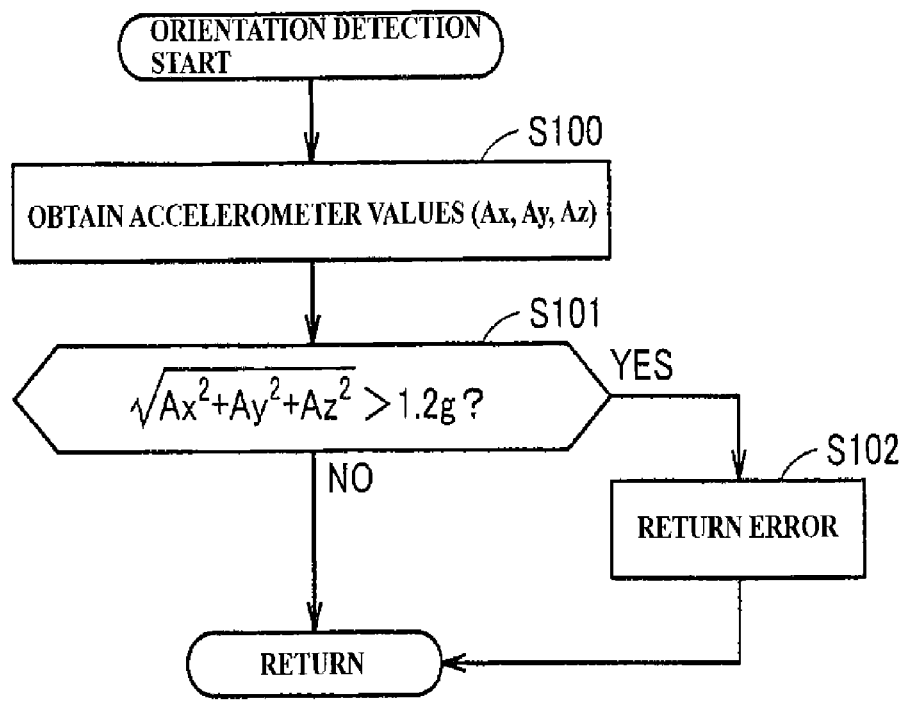
FIG. 11 is a flowchart for detecting an orientation according to the present embodiment.

FIG. 11 is a flowchart illustrating the orientation detection process (S 10).

The orientation detection unit 510 obtains outputs Ax, Ay, and Az for the x, y, and z axes, respectively, from the accelerometer 15 (S100). Ax represents an acceleration component in the x direction, Ay represents an acceleration component in the y direction, and Az represents an acceleration component in the z direction. When the electric toothbrush 1 is at rest (that is, when no dynamic acceleration is acting on the accelerometer 15), a combined vector A of Ax, Ay, and Az corresponds to the gravity acceleration. Here, A=(Ax, Ay, Az) is referred to as an orientation vector.

Here, the magnitude of the orientation vector A=(Ax, Ay, Az) is determined (S101). In the case where it is determined that the orientation vector A=(Ax, Ay, Az) is greater than 1.2 g (where g represents the gravity acceleration) (YES in S101), an error is returned (S102) and the procedure returns to the processing shown in FIG. 10. This is because it is difficult to accurately identify the direction of the gravity acceleration (that is, the three-dimensional orientation of the brush) when a high dynamic acceleration component is present in the accelerometer output. On the other hand, in the case where it is determined that the orientation vector A=(Ax, Ay, Az) is less than or equal to 1.2 g (NO in S101), the processing shown in FIG. 11 ends, and the procedure returns to the processing shown in FIG. 10.

Note that rather than returning an error as in S102, the processes of S100 and S101 may instead be repeated until accelerometer outputs Ax, Ay, and Az from which a combined vector having a magnitude of less than or equal to 1.2 g is obtained. Note also that the threshold value for determining an error is not limited to 1.2 g, and may be a different value instead.

Estimation of Brushing Area

Figure 12:
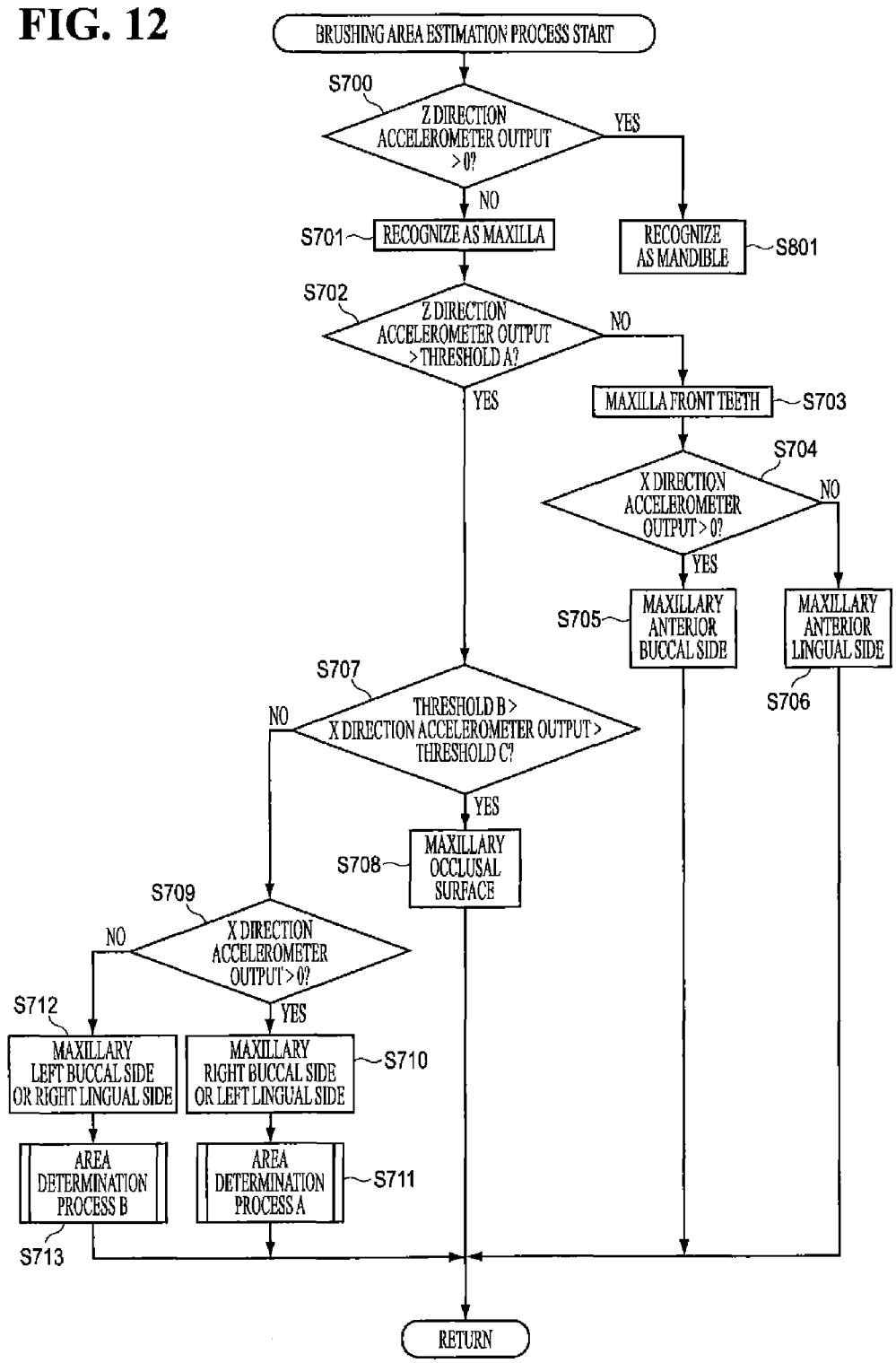
FIG. 12 is a flowchart illustrating details of estimating an area according to the present embodiment.
Figure 13:
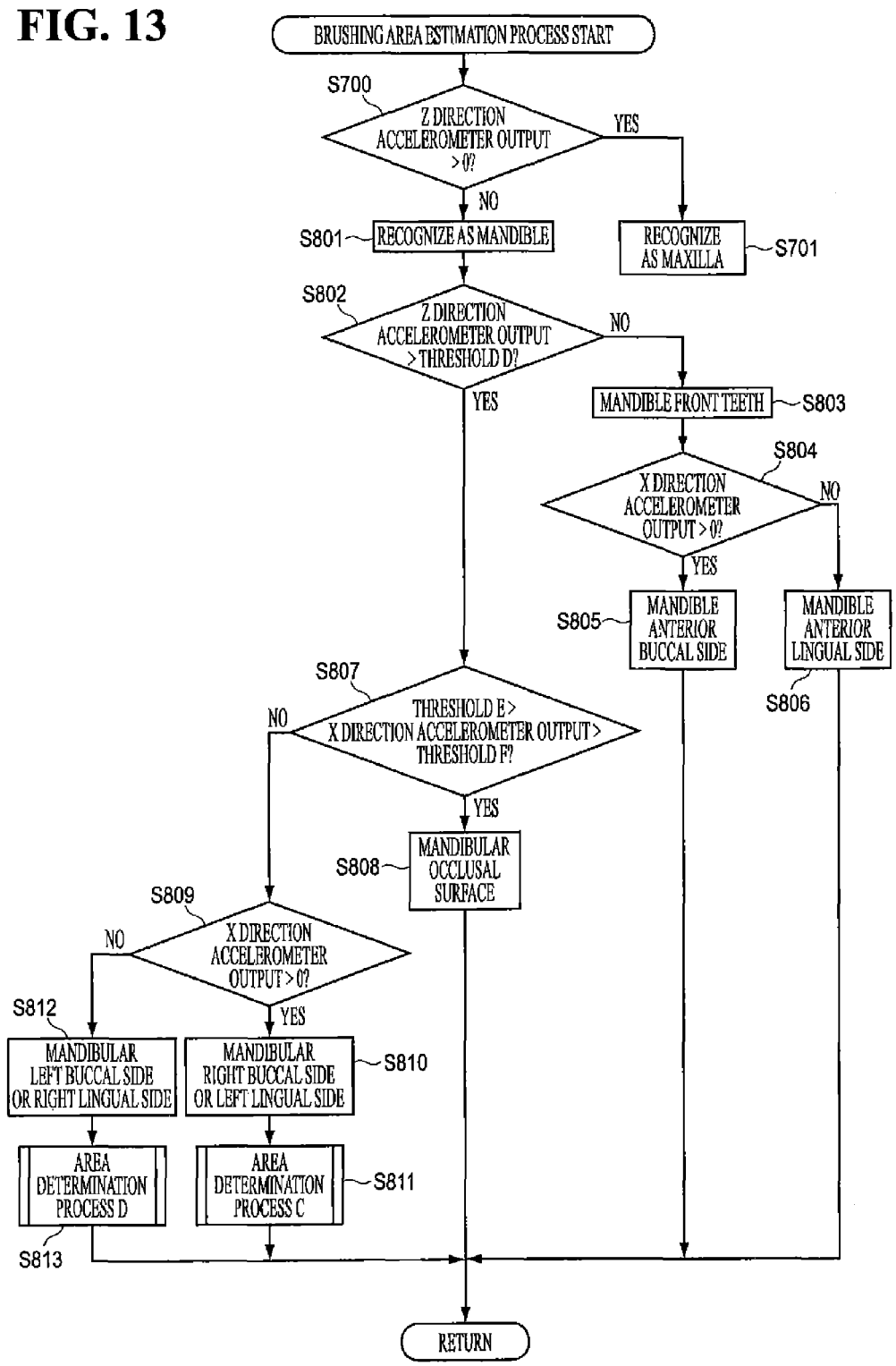
FIG. 13 is a flowchart illustrating details of estimating an area according to the present embodiment.
Figure 14:
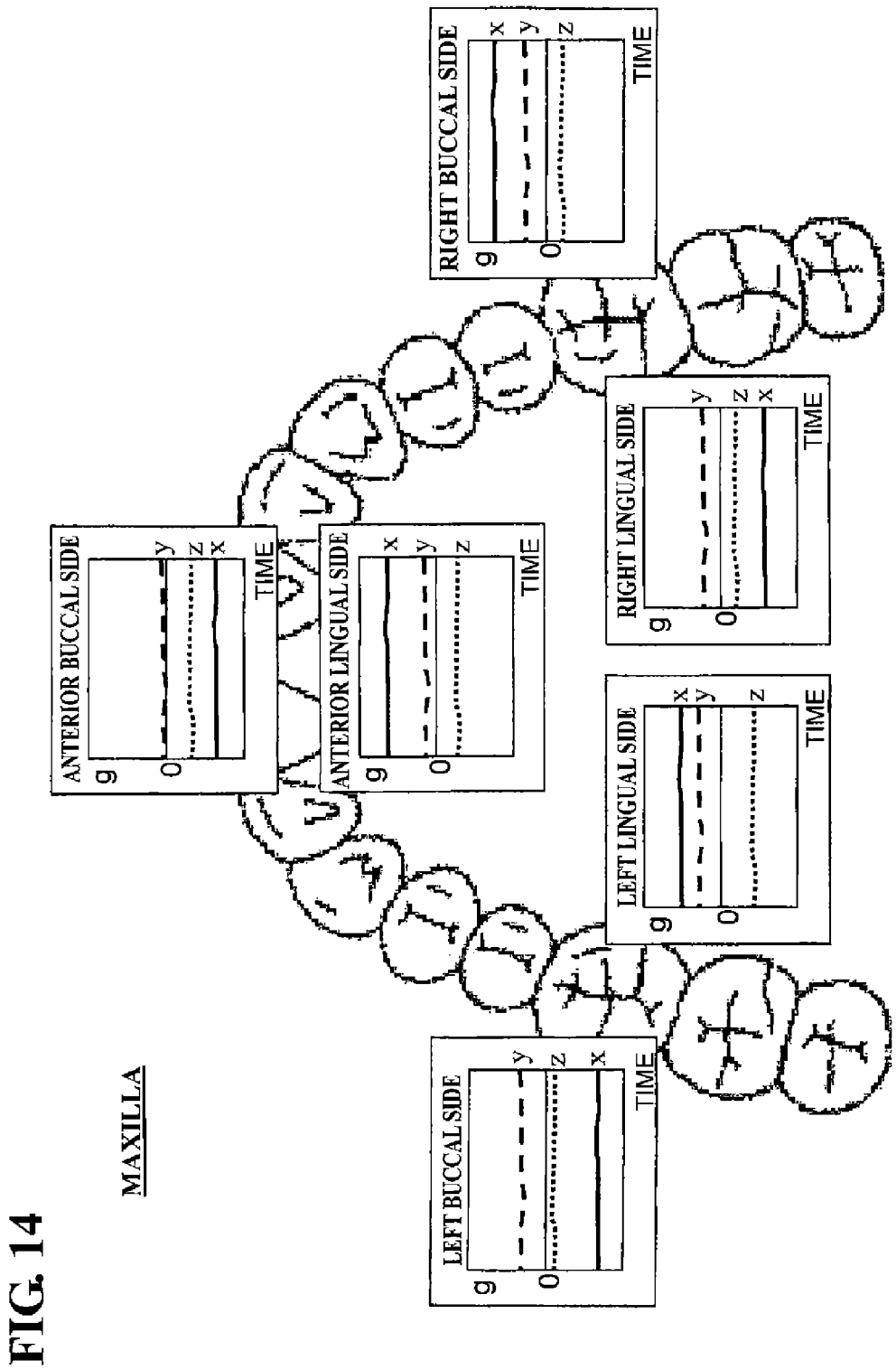
FIG. 14 is a diagram illustrating examples of accelerometer outputs for each brushing area according to the present embodiment.
Figure 15:
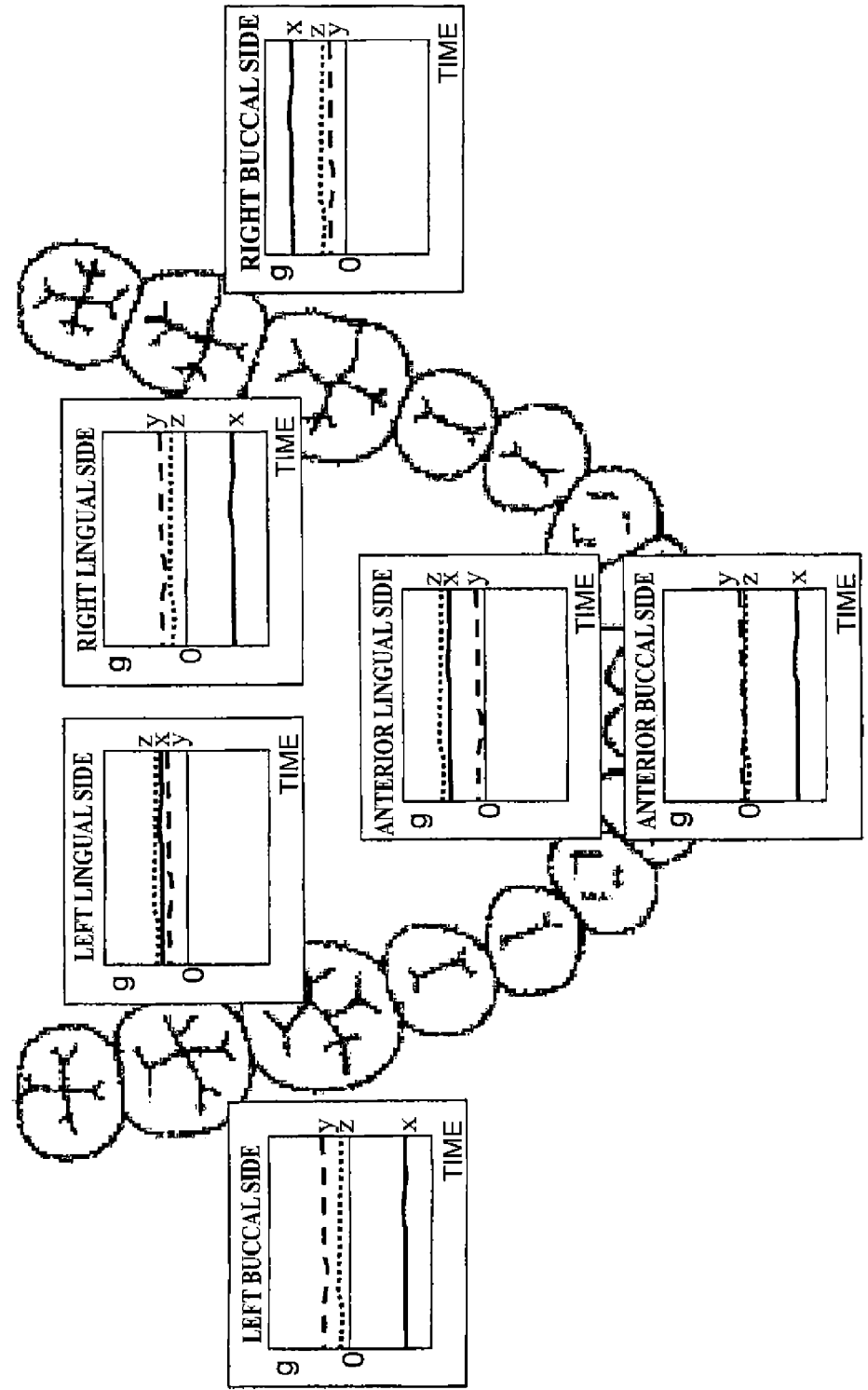
FIG. 15 is a diagram illustrating examples of accelerometer outputs for each brushing area according to the present embodiment.

FIGS. 12 and 13 are flowcharts illustrating the brushing area estimation process (S20) performed by the area estimation unit 520. Meanwhile, FIGS. 14 and 15 are diagrams illustrating examples of accelerometer outputs Ax, Ay, and Az for the respective brushing areas.

First, the CPU 120 determines whether the brushing area is located at the maxilla or the mandible based on the z direction output Az of the accelerometer (S700). This determination focuses on the fact that when the dentition in the maxilla is being brushed, the brush surface is at least pointed upward, whereas when the dentition in the mandible is being brushed, the brush surface is at least pointed downward. In the case where Az>0 (YES in S700), the brushing area is determined to be in the mandible (S801), whereas in the case where Az<0 (NO in S700), the brushing area is determined to be in the maxilla (S701).

(1) Maxilla

The CPU 120 determines whether or not, the brushing area corresponds to the front teeth based on the y direction output Ay of the accelerometer (S702). This determination focuses on the fact that although the main body portion 2 is in a comparatively horizontal state when brushing the front teeth, interference with the lips makes it necessary to tilt the main body portion 2 when brushing the molars. The brushing area is determined to correspond to the front teeth of the maxilla in the case where Ay≤a threshold a (NO in S702) (S703).

In the case where the brushing area has been determined to correspond to the front teeth of the maxilla, the CPU 120 determines whether the brushing area is on the buccal side or on the lingual side based on the x direction output Ax of the accelerometer (S704). This determination focuses on the fact that the brush faces opposite directions on the buccal side and on the lingual side. The brushing area is determined to correspond to the maxillary anterior buccal side in the case where Ax>0 (YES in S704) (S705), whereas the brushing area is determined to correspond to the maxillary anterior lingual side in the case where Ax≤0 (NO in S704) (S706).

Meanwhile, in the case where the brushing area has been determined not to correspond to the front teeth of the maxilla in S702 (YES in S702), the CPU 120 determines whether the brushing area corresponds to the occlusal surface based on the x direction output Ax of the accelerometer (S707). This determination focuses on the fact that the brush surface is approximately horizontal when brushing the occlusal surface and the Ax output is extremely low as a result. In the case where a threshold b>Ax>a threshold c (YES in S707), it is determined that the brushing area corresponds to a maxillary left occlusal surface or a maxillary right occlusal surface (S708). Note, however, that in the present embodiment, no particular distinction is made between the maxillary left occlusal surface and the maxillary right occlusal surface. This is because there is little necessity to change brushing operations between the left and right sides when brushing the occlusal surface.

In the case where Ax≥the threshold b or Ax≤the threshold c (NO in S707), the CPU 120 determines the direction in which the brush surface is facing based on whether or not Ax is greater than 0 (S709). This determination focuses on the fact that the brush surface faces opposite directions on the buccal side and on the lingual side. In the case where Ax>0 (YES in S709), it is determined that the brushing area is the maxillary right buccal side or the maxillary left lingual side (S710), whereas in the case where Ax≤0 (NO in S709), it is determined that the brushing area is the maxillary left buccal side or the maxillary right lingual side (S712).

In the case where the brushing area has been determined to be the maxillary right buccal side or the maxillary left lingual side, the area determination process A is executed (S710, S711). In the case where the brushing area has been determined to be the maxillary left buccal side or the maxillary right lingual side, the area determination process B is executed (S712, S713). The area determination processes A and B will be described later.

(2) Mandible

The CPU 120 determines whether or not the brushing area corresponds to the front teeth based on the y direction output Ay of the accelerometer (S802). This determination focuses on the fact that although the main body portion 2 is in a comparatively horizontal state when brushing the front teeth, interference with the lips makes it necessary to tilt the main body portion 2 when brushing the molars. The brushing area is determined to correspond to the front teeth of the mandible in the case where Ay≤a threshold d (NO in S802) (S803).

In the case where the brushing area has been determined to correspond to the front teeth of the mandible, the CPU 120 determines whether the brushing area is on the buccal side or on the lingual side based on the x direction output Ax of the accelerometer (S804). This determination focuses on the fact that the brush faces opposite directions on the buccal side and on the lingual side. In the case where Ax<0 (YES in S804), the brushing area is determined to correspond to the mandibular anterior buccal side (S805), whereas in the case where Ax≥0 (NO in S804), the brushing area is determined to correspond to the mandibular anterior lingual side (S806).

Meanwhile, in the case where the brushing area has been determined not to correspond to the front teeth of the mandible in S802 (YES in S802), the CPU 120 determines whether the brushing area corresponds to the occlusal surface based on the x direction output Ax of the accelerometer (S807). This determination focuses on the fact that the brush surface is approximately horizontal when brushing the occlusal surface and the Ax output is extremely low as a result. In the case where a threshold e>Ax>a threshold f (YES in S807), it is determined that the brushing area corresponds to a mandibular left occlusal surface or a mandibular right occlusal surface (S808). Note, however, that in the present embodiment, no particular distinction is made between the mandibular left occlusal surface and the mandibular right occlusal surface. This is because there is little necessity to change brushing operations between the left and right sides when brushing the occlusal surface.

In the case where Ax≥the threshold e or Ax≤the threshold f (NO in S807), the CPU 120 determines the direction in which the brush surface is facing based on whether or not Ax is greater than 0 (S809). This determination focuses on the fact that the brush surface faces opposite directions on the buccal side and on the lingual side. In the case where Ax>0 (YES in S809), the brushing area is determined to correspond to the mandibular right buccal side or the mandibular left lingual side (S810), whereas in the ease where Ax≤0 (NO in S809), the brushing area is determined to correspond to the mandibular left buccal side or the mandibular right lingual side (S812).

In the case where the brushing area has been determined to be the mandibular right buccal side or the mandibular left lingual side, the area determination process C is executed (S811). In the case where the brushing area has been determined to be the mandibular left buccal side or the mandibular right lingual side, the area determination process D is executed (S812, S813).

The stated determination algorithm is merely an example, and any determination algorithm may be employed as long as it is capable of detecting a brushing area from the outputs Ax, Ay, and Az of the accelerometer 15. For example, rather than using the values of Ax, Ay, and Az directly as the variables for the determination, two-dimensional variables obtained by combining Ax, Ay, and Az as appropriate may be used in the determination instead. The two-dimensional variables can be set as desired, such as Ay/Az, Ax·Ax+Ay·Ay, Az−Ax, and so on. Alternatively, the brushing area may be determined after converting the acceleration information Ax, Ay, and Az from the respective axes into angle information (orientation angles) $\alpha$, $\beta$, and $\gamma$. For example, the angle of the x axis relative to the gravity acceleration direction may be defined as a roll angle $\alpha$, the angle of the y axis relative to the gravity acceleration direction may be defined as a pitch angle $\beta$, and the angle of the z axis relative to the gravity acceleration direction may be defined as a yaw angle $\gamma$. The thresholds used in the determinations can be set based on the results of clinical experiments or the like.

Area Determination Processes

Processes for determining whether the brushing area corresponds to the buccal side or to the lingual side in the ease where the brushing area has been determined to correspond to the right buccal-side or left-lingual side dentition surface, or to the left buccal-side or right-lingual side dentition surface, will be described. In other words, area determination processes for determining whether the brushing area corresponds to the buccal side or the lingual side (the palatal side) in the case where the brushing area has been determined to correspond to the maxillary right buccal side or maxillary left lingual side, to the maxillary left buccal side or maxillary right lingual side, to the mandibular right buccal side or mandibular left lingual side, or to the mandibular left buccal side or mandibular right lingual side, will be described.

Figure 16:
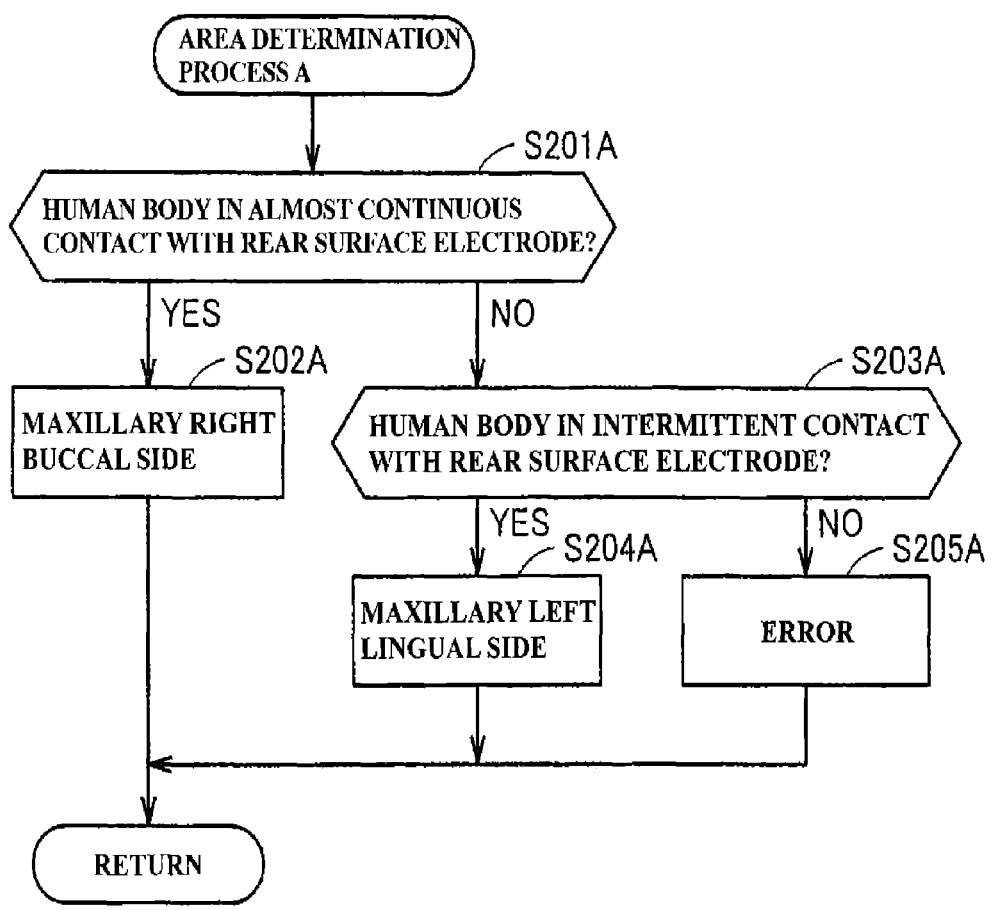
FIG. 16 is a flowchart of an area determination process A according to the present embodiment.

FIG. 16 is a flowchart illustrating the area determination process A.

The area estimation unit 520 determines whether or not the electrode 521 disposed on the rear surface of the brush portion 3 (that is, the rear surface electrode) is in almost continuous contact with the human body (S201A). For example, the CPU 120 determines whether or not the percentage of contact time within a set amount of time is greater than or equal to 80%. Whether or not contact is made with the human body can be determined based on an impedance value detected by the detection portion 54 or based on a change therein.

Figure 17:
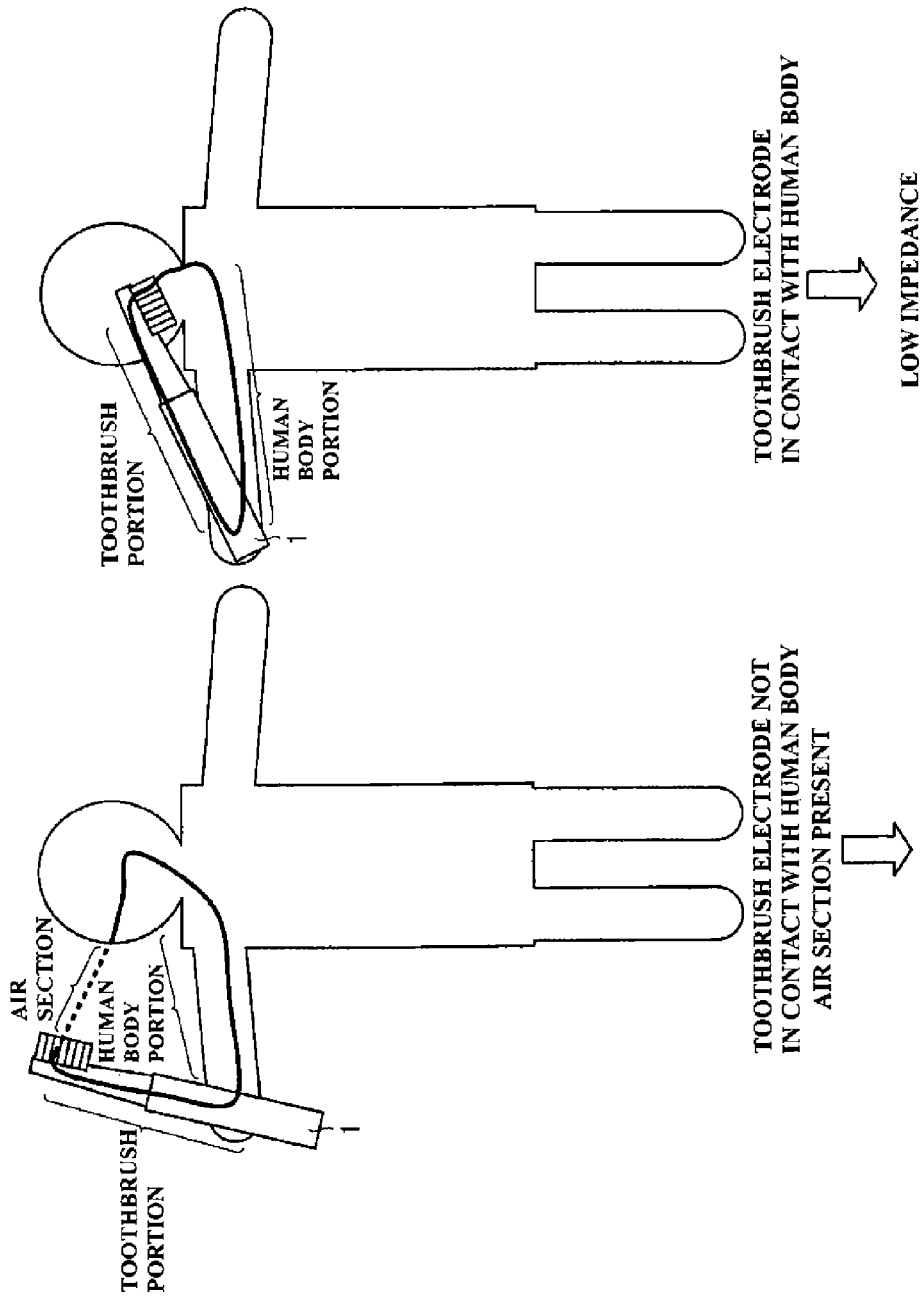
FIG. 17 is a diagram schematically illustrating a circuit passing through the human body in a state in which a rear surface electrode according to the present embodiment is in contact with the human body and a state in which the rear surface electrode is not in contact with the human body.

FIG. 17 is a diagram schematically illustrating a circuit passing through the human body in a state in which the rear surface electrode 521 is in contact with the human body and a state in which the rear surface electrode 521 is not in contact with the human body.

As shown in FIG. 17A, an air section is present when the rear surface electrode 521 is not in contact with the human body, and thus the impedance value is higher than when contact is being made. On the other hand, as shown in FIG. 17B, when the rear surface electrode 521 is in contact with the human body, a closed-loop circuit that passes through the rear surface electrode 521 is configured, and thus the impedance value is lower than when contact is not being made.

Accordingly, whether or not contact is being made can be determined by, for example, detecting whether or not the impedance value is greater than or equal to a predetermined threshold. The impedance threshold is determined in advance through experimentation.

In the case where it has been determined that the rear surface electrode 521 is in almost constant contact with the human body (YES in S201A), it is determined that the brushing area corresponds to the maxillary right buccal side (S202A). This is because the rear surface of the brush portion 3 in the electric toothbrush 1 is in almost constant contact with the inner cheek when brushing on the buccal side.

On the other hand, in the case where it has been determined that the rear surface electrode 521 is not in almost constant contact with the human body (NO in S201A), it is furthermore determined whether or not the rear surface electrode 521 is in intermittent contact with the human body (S203A). For example, the CPU 120 determines whether or not the percentage of contact time within a set amount of time is greater than or equal to 30% and less than 80%. In the case where it has been determined that the rear surface electrode 521 is in intermittent contact with the human body (YES in S203A), it is determined that the brushing area corresponds to the maxillary left lingual side (S204A). This is because the rear surface of the brush portion 3 in the electric toothbrush 1 makes contact with the tongue intermittently when brushing the lingual side (the palatal side).

In the case where it has been determined that the rear surface electrode 521 is not making intermittent contact with the human body (NO in S203A), an error is determined to have occurred (S205A).

Figure 18:
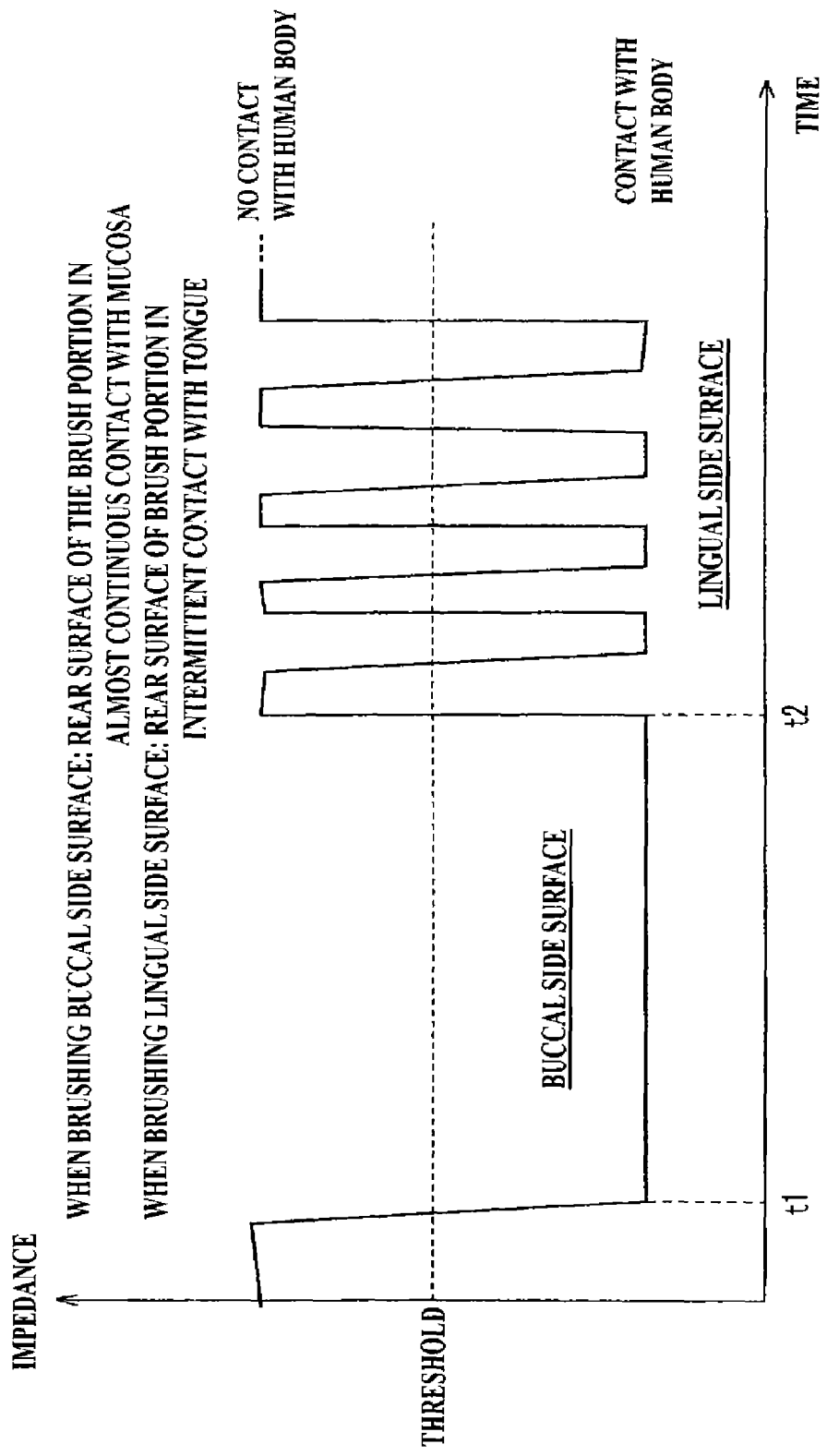
FIG. 18 is a diagram illustrating a specific example of a method for determining between a buccal side/a lingual side according to the present embodiment.

A specific example of the method for determining between the buccal side/lingual side according to the present embodiment is illustrated in FIG. 18. Note that in order to obtain impedance levels such as those shown in FIG. 18, for example, a pair of electrodes for current application and a pair of electrodes for voltage detection, as are employed in body fat meters, may be provided on the rear surface of the brush portion 3.

Referring to FIG. 18, the impedance value is constantly less than the threshold from time t1 to t2, and thus the brushing area is determined to be the buccal-side surface. However, from time t2, the impedance value intermittently rises above the threshold, and thus the brushing area is determined to be the lingual-side surface.

Figure 19:
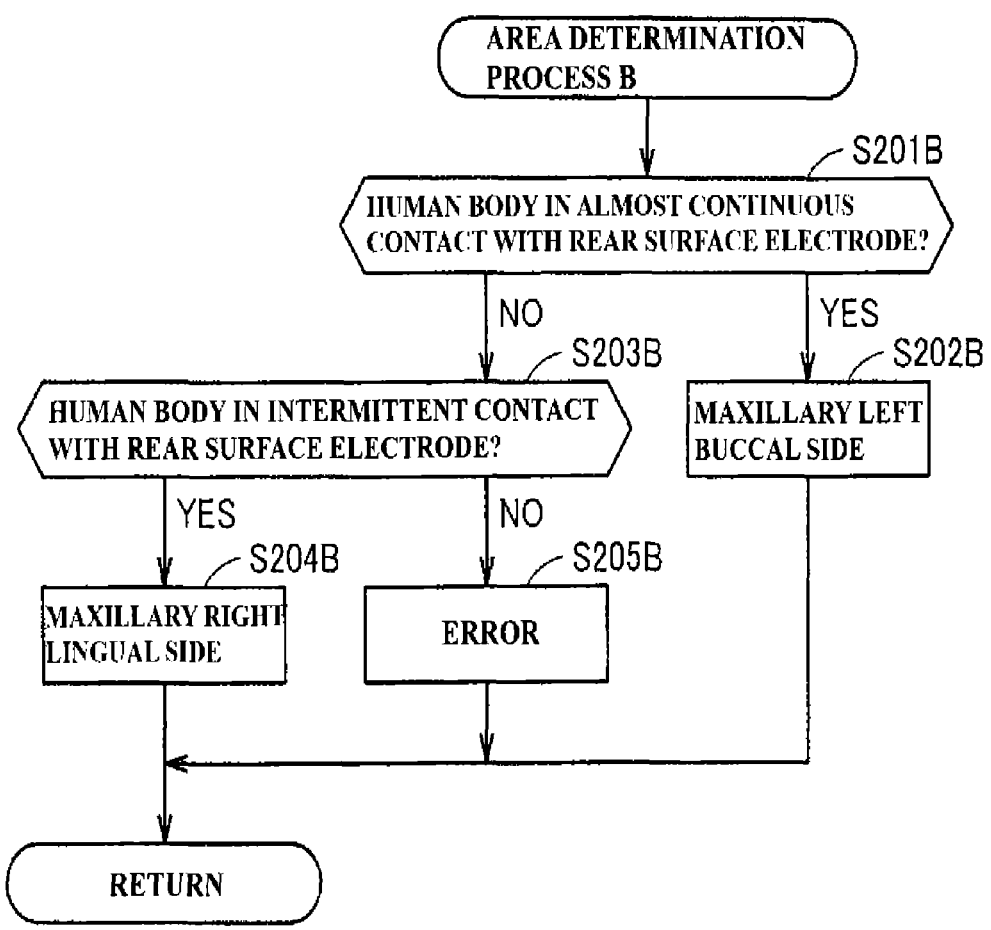
FIG. 19 is a flowchart of an area determination process B according to the present embodiment.
Figure 20:
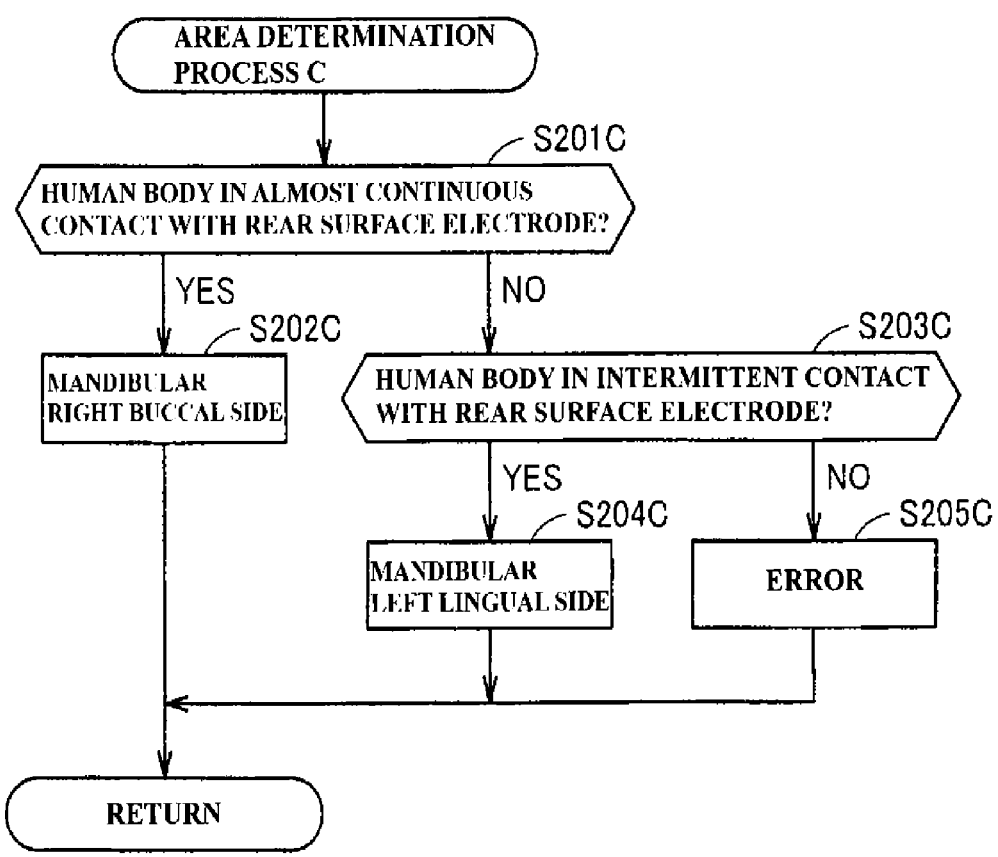
FIG. 20 is a flowchart of an area determination process C according to the present embodiment.
Figure 21:
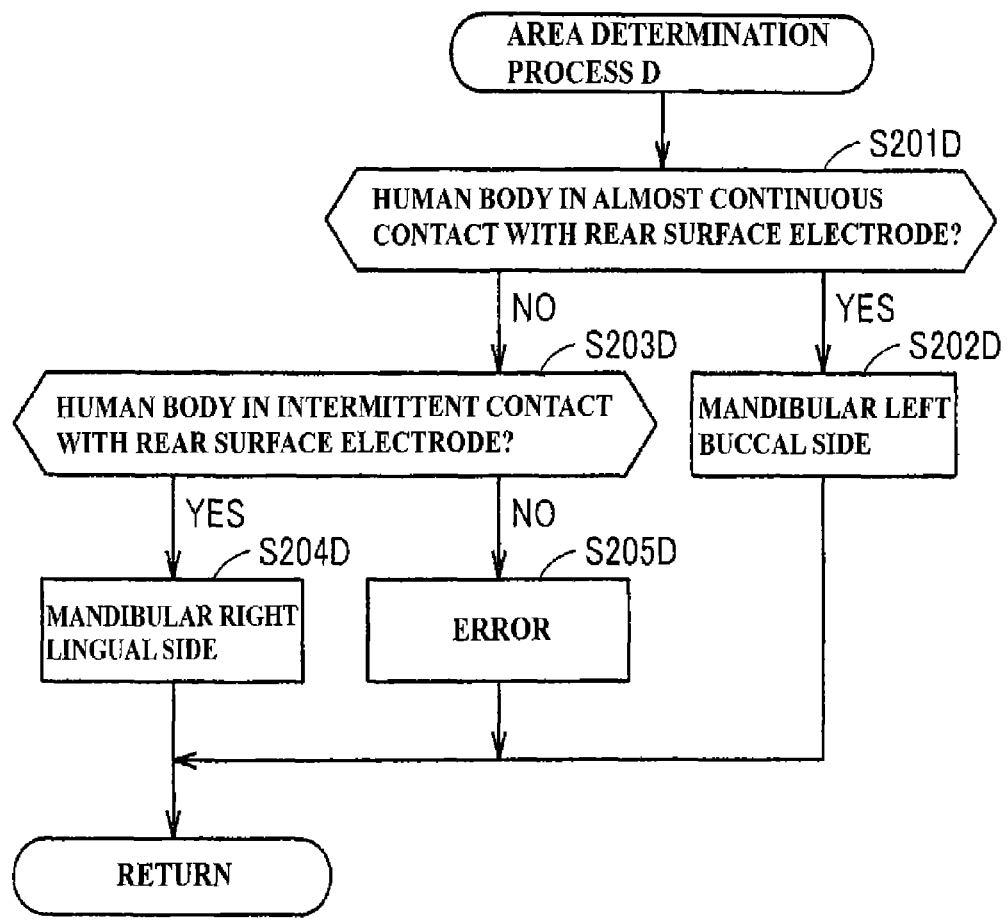
FIG. 21 is flowchart of an area determination process D according to the present embodiment.

FIGS. 19 through 21 are flowcharts illustrating the area determination processes B, C, and D, respectively. The processes illustrated in these flowcharts are basically the same as the area determination process A shown in FIG. 16. The differences lie in that the maxillary right buccal side (S202A) and the maxillary left lingual side (S204A) shown in FIG. 16 differ based on the general area determination results prior to moving to the area determination processes. Specifically, in the area determination process B shown in FIG. 19, the brushing areas are determined to be the maxillary left buccal side (S202B) and the maxillary right lingual side (S204B), respectively, instead of the maxillary right buccal side (S202A) and the maxillary left lingual side (S204A) in the area determination process A shown in FIG. 16. With the area determination process C shown in FIG. 20, the brushing areas are determined to be the mandibular right buccal side (S202C) and the mandibular left lingual side (S204C), respectively, instead of the maxillary right buccal side (S202A) and the maxillary left lingual side (S204A) in the area determination process A shown in FIG. 16. With the area determination process D shown in FIG. 21, the brushing areas are determined to be the mandibular left buccal side (S202D) and the mandibular right lingual side (S204D), respectively, instead of the maxillary right buccal side (S202A) and the maxillary left lingual side (S204A) in the area determination process A shown in FIG. 16.

S201B, S203B and S205B shown in FIG. 19 are similar processes to S201A, S203A and S205A shown in FIG. 16. S201C, S203C and S205C shown in FIG. 20 are similar processes to S201A, S203A and S205A shown in FIG. 16. S201D, S203D and S205D shown in FIG. 21 are similar processes to S201A, S203A and S205A shown in FIG. 16.

Through the stated processes, the current brushing area is determined to be one of the maxillary anterior buccal side (S705), the maxillary anterior lingual side (S706), the maxillary occlusal surface (S708), the maxillary right buccal side (S202A), the maxillary left lingual side (S204A), the maxillary left buccal side (S202B) or maxillary right lingual side (S204B), the mandibular anterior buccal side (S805), the mandibular anterior lingual side (S806), the mandibular occlusal surface (S808), the mandibular right buccal side (S202C), the mandibular left lingual side (S204C), the mandibular left buccal side (S202D), and the mandibular right lingual side (S204D).

Figure 10:
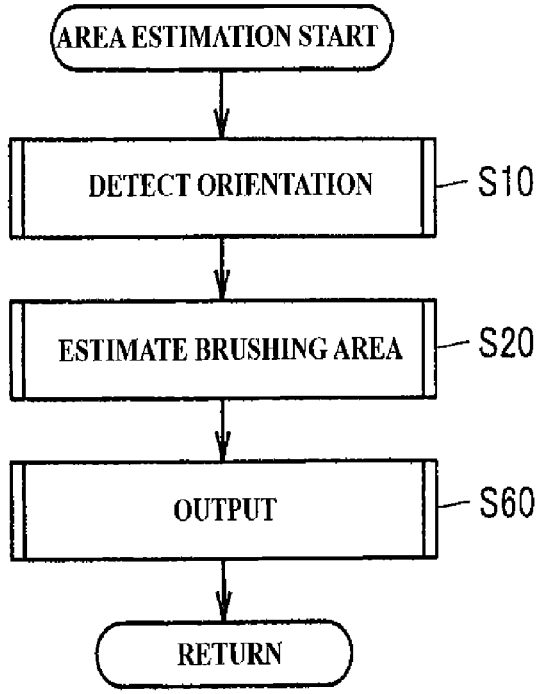
FIG. 10 is a main flowchart for estimating areas according to the present embodiment.

Note that in the present embodiment, the determination between the buccal side and the lingual side is carried out by detecting impedance values in a set amount of time, and thus the result of the determination between the buccal side and the lingual side may be first obtained after performing multiple cycles of the brushing area estimation process (S20 in FIG. 10).

In addition, because the amount of plaque is not outputted for the occlusal surface in the present embodiment, the area determination for the occlusal surface may be omitted.

When the area is estimated as described above, the processing returns to FIG. 9. Referring to FIG. 9, the CPU 120 compares the area that is indicated by information that is estimated immediately before and stored in the memory 121 with an area that is currently output by the area estimation unit 520, and determines whether or not the brushing area has changed, based on the comparison result (step T5). Based on the determination result, while it is not determined that the brushing area has moved to another area (NO in step T5), the processing of step T3 is repeated, whereas if it is determined that the brushing area has moved to another area (YES in step T5), the processing moves to step T7.

The CPU 120 determines whether or not the user operates the switch 403, based on an operation signal output by the operation reception unit 505 (step T7). If it is determined that the user does not operate the switch 403 (NO in step T7), the processing returns to step T3, and the subsequent processes are similarly repeated.

On the other hand, if it is determined that the user operates the switch 403 (YES in step T7), a process for detecting the amount of plaque (a routine RT) is executed.

First, based on the output of the accelerometer 15, the orientation detection unit 510 determines whether or not the user turns his/her hand that is holding the electric toothbrush 1 such that the rear surface of the surface in which the brush 210 is implanted opposes the brushing area (step T9). In other words, the orientation detection unit 510 determines whether or not a difference between the direction of the previous orientation vector A=(Ax, Ay, Az) detected in step T3 and the direction of an orientation vector A=(Ax, Ay, Az) detected in step T7 when the switch 403 is turned on is in the range of a predetermined angle, and thereby determines whether or not the user turns his/her hand that is holding the toothbrush.

If it is determined that the difference is in the range of a predetermined angle, that is, if it is determined that the user has not turned his/her hand (NO in step T9), the process of step T9 is repeated until the fact that the user turns his/her hand is detected, whereas if it is determined that the difference is not in the range of a predetermined angle, that is, if it is determined that the user turned his/her hand that was holding the electric toothbrush 1 (YES in step T9), the processing moves to step T11.

In step T11, in a state in which the rear surface of the surface in which the brush 210 is implanted opposes the brushing area as a result of turning his/her hand that is holding the electric toothbrush 1, the image capture unit 530 controls the LED 400 so as to cause light to be emitted (step T11). During a period from when light starts to be emitted to when image capture ends, the drive control unit 500 outputs a control signal for stopping the movement of the vibrating member 5. Accordingly, a drive signal that stops the rotation of the motor 10 is supplied from the drive signal supply unit 580 thereto (step T13). In this manner, as a result of the stopping of the rotation of the motor 10 and brushing, it is possible to notify the user that the brush is disposed in a predetermined area, it is a time to capture an image, and the brush is inhibited from moving.

Note that in order to prevent image obtained by image capture from being blurred, that is, in a period of image capture, in order to make it possible to sufficiently irradiate an area whose plaque amount is to be detected with light and to make a sufficient amount of the reflected light capable of entering the CCD 401, the drive signal is not necessarily a signal that stops the movement, and it may be a signal that suppresses the movement. For example, the drive signal may be a signal that changes the period or the Duty ratio specified by the control signal to extend the period of the periodic movement of the brush 210 that is synchronized with the rotation of the motor 10. More specifically, in the case where the periodic movement is the reciprocating movement of a vertical travel or a horizontal travel, a time period required for one round trip is extended, and in the case of rotational movement, a time period required for one rotation is extended.

Also, blurring in an image obtained by image capture may be corrected by image processing, instead of changing the period of movement.

In a period in which the periodic movement of the brush 210 is stopped or suppressed in this manner, of the light emitted from the LED 400, light including the light reflected from plaque is received by the CCD 401, and then an image signal is derived through photoelectric conversion. The image capture unit 530 obtains image data from the image signal (steps T15, T17).

If image data is obtained and image capture ends, the drive control unit 500 returns the period or the Duty ratio specified by the control signal to the original value. Accordingly, the period of the periodic movement of the brush 210 that is synchronized with the rotation of the motor 10 returns to the original value (step T19). When the period of movement returns to the original value, the user can brush the next area by turning his/her hand that is holding the electric toothbrush 1 so that the brush 210 opposes the brushing area.

If the image data is obtained by image capture described above, the plaque detection unit 540 detects the amount of plaque in the area estimated in step T3, based on the image data sent from the image capture unit 530 (step T21). If the amount of plaque is detected, the storage unit 550 stores in the table TB 1 the detected amount of plaque in association with the area estimated in step T3 and data on time measured by the timer 122 (step T23).

Thereafter, based on the data of the table TB1, the CPU 121 determines whether or not the detection of the amounts of plaque ends for all of the areas shown in FIG. 8 (step T25). If it is determined that there is an area in which the amount of plaque is not detected (NO in step T25), the processing returns to step T3, and the processing for the next area is similarly performed, whereas if it is determined that the amounts of plaque are detected for all of the areas (YES in step T25), the processing moves to step T27.

In step T27, information stored in the table TB1 by processes in steps T3 to T25 is read out by the readout unit 560 at this time of brushing, and the information is displayed by the display control unit 570 in the display 111 of the display device 110 via the data transmission unit 123 (step T27).

Figure 22:
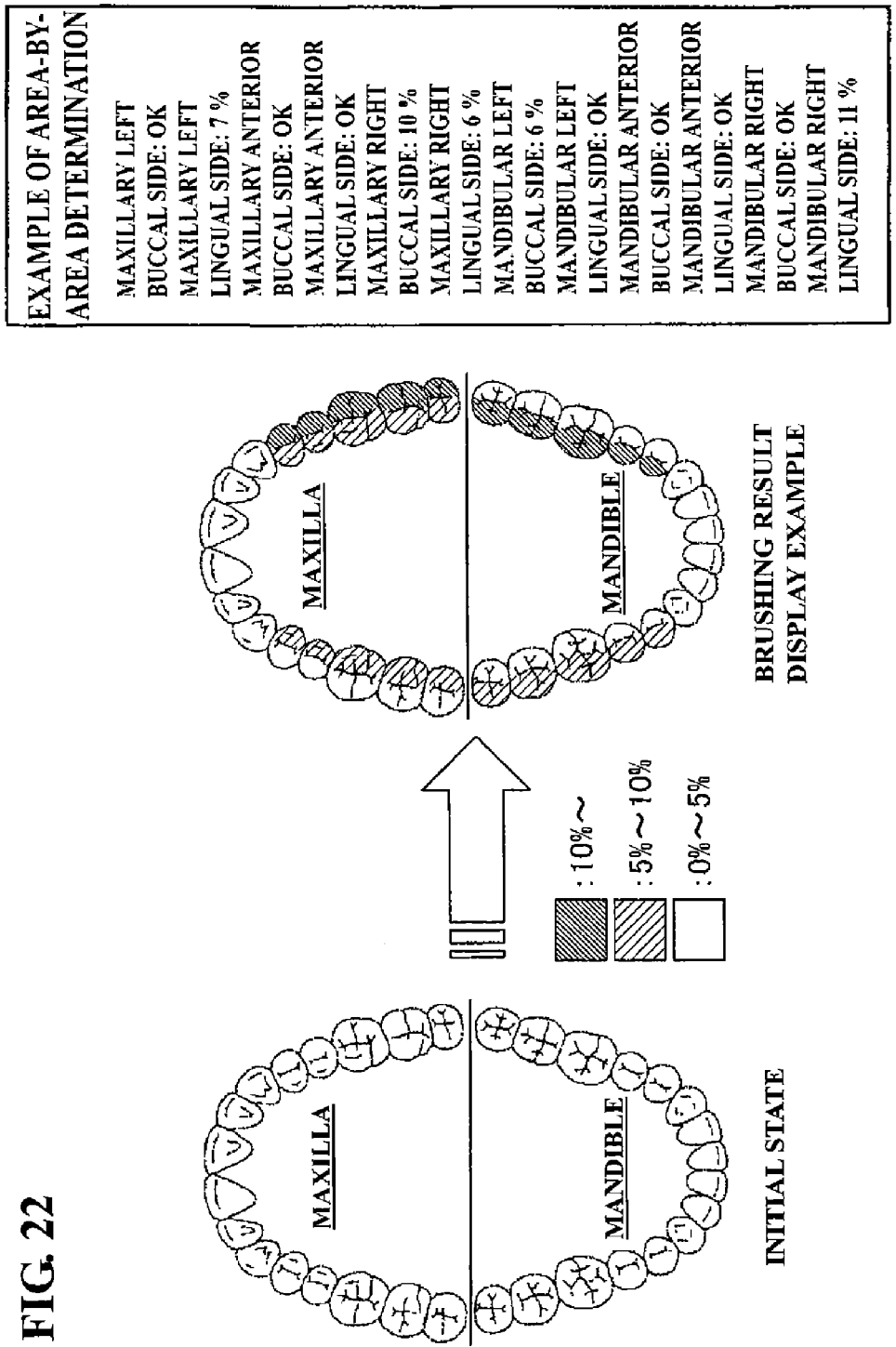
FIG. 22 is a diagram illustrating an example of display according to the present embodiment.

An example of display in step T27 is shown in FIG. 22. The display control unit 570 reads out the amount of plaque in each area from the table TB1 of the memory 121 by the readout unit 560, and ranks the amount of plaque as for example, "0 to 5%", "5 to 10%", and "above 10%", and evaluates only. "0 to 5%" as "OK". These ranking and evaluation results are then sent to the display device 110. The dentition is displayed in the display 111 of the display device 110, and the areas within the dentition are lighted by a color that corresponds to the ranking of plaque amount ("OK" by white, "5 to 10%" by yellow, "above 10%" by red, and so on). By viewing this display, the user can intuitively grasp which area of the dentition still has plaque and which area of the dentition has not been brushed enough.

Note that ranking and evaluation results may be displayed by the display control unit 570 in the display 111 of the display device 110 via the data transmission unit 123, each time an area is estimated at the time of brushing.

When the user checks the area in which plaque remains from the display shown in FIG. 22 and brushes the area, similarly to step T3, the brushing area is estimated by the orientation detection unit 510 and the area estimation unit 520 (step T29). If the area is estimated, the display control unit 570 gives a notification about continuing brushing using the area in the display 111 shown in FIG. 22 being displayed in a blinking manner (step T31). Accordingly, the user is urged to continue brushing in order to remove plaque in the area during a blinking period (for example, 10 seconds).

Also, a drive signal for reliably removing plaque in the area estimated in step T29 is supplied to the motor 10 (step T35). Specifically, the readout unit 560 searches the table TB1 based on the area estimated in step T29, and reads out from the table TB1 the amount of plaque stored most recently among the amounts of plaque that correspond to the area, based on the result of the search. The readout unit 560 then reads out data corresponding to the amount of plaque based on the amount of plaque that is read out, from the table TB2 (step T33). The drive control unit 500 outputs a control signal based on the data that is read out.

Figure 23:
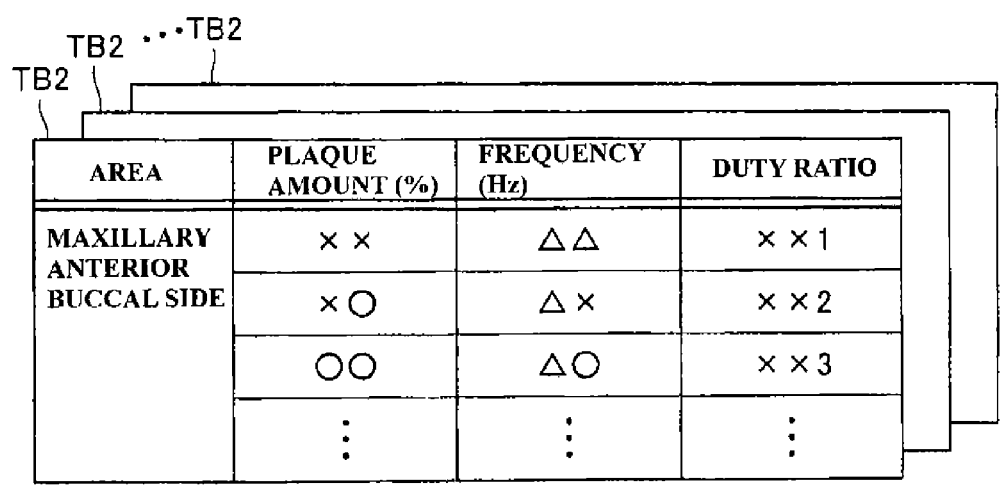
FIG. 23 is a diagram illustrating a table that stores data on drive signals for removing the amount of plaque with regard to each area according to the present embodiment.

As shown in FIG. 23, the table TB2 is stored in the memory 121 for each area in advance. The data of the table TB2 is prepared by experimentation. With regard to the corresponding area, for each of the amounts of plaque, a frequency (unit: Hz) and a Duty ratio for determining the period of a drive signal for removing the amount of plaque are stored in the table TB2.

Accordingly, in a predetermined period in which a notification is given in step T31, the user can brush a desired area in response to a drive signal that is based on an appropriate period and a Duty ratio for removing the plaque in the area. In other words, the period of brushing that is a periodic movement of the brush 210 is appropriately changed in order to remove plaque in a desired area.

The CPU 120 determines whether or not the switch 403 is operated, based on the output of the operation reception unit 505 (step T37). If it is determined that the switch 403 is not operated (NO in step T37), the processing returns to step T35, and brushing continues. On the other hand, if the user desires to check the amount of plaque when he/she thinks that plaque in a desired area may be removed after the end of the blinking display described above or the like, he/she operates the switch 403 (YES in step T37).

If the switch 403 is operated, the routine RT including steps T9 to T21 described above is executed. Accordingly, the amount of plaque with respect to the area estimated in step T29 after brushing is detected, and information of the table TB1 corresponding to the area is updated using the detected amount of plaque, and the detected amount of plaque in the area (the amount of plaque after the update) is displayed in the display 111 (step T39). The user can determine from the display whether or not he/she was able to remove the unbrushed plaque.

After the amount of plaque is displayed, the area estimation process is performed (step T41). Based on the result of the estimation, it is determined whether or not the user has changed the brushing area to another area (step T43). If it is determined that he/she has changed the brushing area to another area (YES in step T43), the processing returns to step T31, and the subsequent processes are similarly repeated. On the other hand, if it is determined that the area has not changed (NO in step T43), the CPU 120 determines whether or not the switch 402 is operated to turn off the power source based on the output of the operation reception unit 505, and stopping of the brushing movement is required (step T45).

If it is determined that stopping of the brushing movement is not required (NO in step T45), the processing returns to step T41, and the subsequent processes are similarly repeated, whereas if it is determined that stopping of the brushing movement is required (YES in step T45), the drive control unit 500 outputs a control signal for stopping brushing. Accordingly, the drive signal supply unit 580 stops supplying a drive signal to the motor 10, and the motor 10 stops (step T47). This ends the processing shown in FIG. 9.

Note that although the electric toothbrush 1 includes the plaque detection unit 540 and the table TB1 in FIG. 6, the MPU 113 of the display device 110 may include them in place of the electric toothbrush 1, or both the electric toothbrush 1 and the MPU 113 may include them.

Another Embodiment

Although according to this embodiment, it is assumed that if the switch 403 for giving an instruction to detect plaque is operated (YES in step T7), the detection of a plaque amount is started, a configuration may be adopted in which if a change of brushing area is detected instead of the operation of the switch 403, the detection of a plaque amount is started. Also, in this embodiment, although a determination about turning a user's hand is required in step T9 in the case where the LED 400 and the CCD 401 are mounted in the mode shown in FIG. 2, in the case where they are mounted in the mode shown in FIG. 5 instead of the mode in FIG. 2, it is possible to omit a determination about turning a user's hand.

In either case, the LED 400 emits light only in a period of image capture, and image capture including emission of light from the LED 400 is stopped in a period from when image capture ends to when it is detected that the brushing area moves, as a result of which it is possible to suppress the amount of power consumption.

Although it is assumed that the amount of plaque is detected after the area is estimated in FIG. 9, plaque detection may be performed independently of area estimation. In other words, a configuration may be adopted in which if the user operates the switch SW so that the operation reception unit 505 inputs an instruction to capture an image, the image capture unit 530 captures an image in accordance with the image capture instruction. Accordingly, a configuration may be adopted in which when said operation is performed, the image of an area against which the brush 210 is pressed is captured, the amount of plaque is detected, and the detection result is displayed in the display 111 (and/or the captured image is displayed).

Also, although it is assumed that a process for recording the amounts of plaque in all of the areas in the table TB1 (steps T3 to T25) and then a process for brushing to remove plaque (steps T27 to T47) based on the recording result are successively performed in FIG. 9, the order of processes is not limited to this.

In other words, a configuration may be adopted in which in the case where information is stored in the table TB1 in advance, a process for brushing to remove plaque (steps T27 to T47) based on the information is performed when an operation is performed to turn on the power source. In this case, the CPU 120 detects, among all of the areas, an area in which the amount of plaque is not evaluated as "OK" and the amount of plaque does not change for a predetermined period (for example, for the last three days) based on the information of the table TB1, and displays the result of the detection in the display 111 of the display device 110 as a guide as in FIG. 22. Accordingly, it can be determined that the user has a habit of not brushing the area. For example, in the case where he/she usually uses a hand toothbrush and sometimes uses the electric toothbrush 1, the CPU 120 compares the amount of plaque detected previously with the amount of plaque currently detected in each area, and is capable of determining, based on the comparison result, that the area in which the amount of plaque does not change is an area in which plaque is not removed by hand brushing. Therefore, it is possible to display a guidance that the area is always insufficiently brushed (the user has a habit of not brushing the area) via the display device 110.

Also, a configuration may be adopted in which when the brushing area of the electric toothbrush 1 is determined to be the area that is not brushed, the display device 110 gives a notification about the area being an important brushing point ("please continue to brush this tooth for ten seconds").

Also, a configuration may be adopted in which the table TB1 for each user is read out from the memory 121, is transmitted by the data transmission unit 123 to an external computer (a server device) (not shown), and is managed in a memory of the external computer. If the memory of the external computer is accessed by a dentist, the dentist can easily plan regular dental advice and appropriate treatment for each user, based on the information in the table TB1 for each user.

The embodiments and variations disclosed herein are to be understood in all ways as exemplary and in no ways limiting. The technical scope of the present invention is defined by the appended claims not by the description given above, and all variations that fall within the meaning and range of equivalency of the claims are intended to be embraced therein.

REFERENCE SIGNS LIST 1 electric toothbrush
2 main body portion
3 brush portion
4 shank portion
5 vibrating member
10 motor
11 rotating shaft
12 driving circuit
13 rechargeable battery
14 coil
15 accelerometer
20 stem portion
21 brush component
30 eccentric shaft
50 contact detection unit
52 electrode portion
54 detection portion
61, 62, 63, 521, 522 electrode
64, 65 lead wire
100 charger
110 display device
111 display
112 data receiving unit
121 memory
122 timer
123 data transmission unit
202 elastic member
203 shaft bearing
210 brush
402, 403 SW switch
500 drive control unit
505 operation reception unit
510 orientation detection unit
520 area estimation unit
521 rear surface electrode
522 main body electrode
530 image capture unit
540 plaque detection unit
550 storage unit
560 readout unit
570 display control unit
580 drive signal supply unit
600 end

The invention claimed is:

1. An oral care apparatus comprising:
a care member for caring for an oral cavity;
an orientation detection unit that detects an orientation of the care member;
an area estimation unit that estimates a care area in the oral cavity, based on the detected orientation;
a light source that emits light having a predetermined wavelength to which plaque reacts;
a photoelectric conversion unit that receives light and converts the received light into an electric signal;
an image capture unit that causes the light source to irradiate the care area with light, and that obtains image data, based on the electric signal of light reflected from the care area that is converted by the photoelectric conversion unit;
a plaque detection unit that detects an amount of plaque in the care area, based on the image data obtained by the image capture unit; and
a storage unit that is configured to store, in a memory, the care area estimated by the area estimation unit and the amount of plaque in the care area detected by the plaque detection unit in association with each other.

2. The oral care apparatus according to claim 1, further comprising:
a drive unit that causes the care member to periodically move; and a drive control unit that controls the drive unit,
wherein the drive control unit controls, when the image capture unit causes the light source to emit light, the drive unit such that a period of movement of the care member is extended.

3. The oral care apparatus according to claim 1, further comprising:
a drive unit that causes the care member to periodically move; and
a drive control unit that controls the drive unit,
wherein the drive control unit controls, when the image capture unit causes the light source to emit light, the drive unit such that movement of the care member stops.

4. The oral care apparatus according to claim 2,
wherein the drive control unit controls the drive unit such that the period is changed based on the amount of plaque stored in the memory in association with the care area estimated by the area estimation unit.

5. The oral care apparatus according to claim 4, wherein the drive unit periodically vibrates the care member.

6. The oral care apparatus according to claim 4, wherein the drive unit periodically rotates the care member.

7. The oral care apparatus according to claim 1, further comprising:
an operation reception unit that receives an operation for giving an instruction to capture an image,
wherein the image capture unit causes, when the operation reception unit receives an operation, the light source to emit light.

8. The oral care apparatus according to claim 1, which displays image data output by the image capture unit, in a display unit.

9. The oral care apparatus according to claim 1, which displays the amount of plaque in the care area detected by the plaque detection unit, in a display unit.

10. The oral care apparatus according to claim 1, which displays information stored in the memory, in a display unit.

11. The oral care apparatus according to claim 1, further comprising:
an attachment surface for attaching the care member,
wherein a light emitting surface of the light source and a light receiving surface of the photoelectric conversion unit are provided on a rear surface of the attachment surface.

\* \* \* \* \*